(12) United States Patent
Ishikawa et al.

(10) Patent No.: US 6,308,572 B1
(45) Date of Patent: Oct. 30, 2001

(54) GAS CONCENTRATION SENSOR

(75) Inventors: Hideki Ishikawa; Yoshikuni Sato; Keigo Banno, all of Aichi; Noboru Ishida, Gifu; Takafumi Oshima, Aichi, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/504,118

(22) Filed: Feb. 15, 2000

(30) Foreign Application Priority Data

Feb. 15, 1999 (JP) .................................................. 11-036425
Feb. 17, 1999 (JP) .................................................. 11-038799
Jul. 12, 1999 (JP) .................................................. 11-198028

(51) Int. Cl.$^7$ ............................. G01H 5/00; G01N 29/02

(52) U.S. Cl. ........................................... 73/597; 73/24.01

(58) Field of Search ................................. 73/597, 24.01, 73/24.05, 24.06, 116, DIG. 1, 32 A, 23.31

(56) References Cited

U.S. PATENT DOCUMENTS

| 4,787,252 | 11/1988 | Jacobson et al. .................. 73/861.28 |
| 5,247,826 | * 9/1993 | Frola et al. ........................... 73/24.01 |
| 5,909,535 | * 5/1999 | Doe ........................................... 73/32 |
| 6,167,747 | * 1/2001 | Koch et al. ............................. 73/19.03 |

FOREIGN PATENT DOCUMENTS

| 8-105865 | 4/1996 | (JP) ................................. G01N/29/18 |
| 8-94593 | 4/1996 | (JP) ................................. G01N/29/18 |

OTHER PUBLICATIONS

M. Sultan et al, "Closed Loop Canister Purge Control System", SAE Paper 980206.
M. Habaguchi et al, Proceedings for Society of Automotive Engineers of Japan 955, Sep. 1995, "Gasoline Vapor Concentration Sensor—On Board Measurement by Ultrasonic Pulse—", accompanied by an English language translation.

* cited by examiner

*Primary Examiner*—Richard A. Moller
(74) *Attorney, Agent, or Firm*—Sughrue, Mion, Zinn, Macpeak & Seas, PLLC

(57) ABSTRACT

A gas concentration sensor comprises an ultrasonic element 33 opposite a reflection surface 34. A depression 34a is formed on an edge portion of a reflection surface 34 which is in contact with a side wall of a measurement chamber 32 such that a bottom surface of the depression 34a is substantially in parallel with the reflection surface 34. The distance between the ultrasonic element 33 and the edge portion of the reflection surface 34 becomes greater than the distance between the ultrasonic element 33 and a central portion of the reflection surface 34. As a result, an indirect wave, which impinges obliquely on the side wall of the measurement chamber 32 and propagates along the side wall, is reflected from the bottom surface of the depression 34a and propagates. Thus, the propagation distance of this indirect wave becomes greater as compared to the case where the reflection surface 34 is flat, so that the indirect wave is not combined with a direct wave in the vicinity of a modulation point of the direct wave. That is, since the modulation point of the direct wave can be detected accurately, a time interval between a modulation point of a transmitted wave and that of a received wave can be measured as the propagation time of an ultrasonic wave, thereby enabling accurate determination of gas concentration.

45 Claims, 18 Drawing Sheets

Gas Concentration Sensor 25

Ultrasonic Transmitter-Receiver Element 33

Gas Concentration Sensor

— Transmitted Waveform

— Received Waveform

Purge Gas

— Transmitted Waveform

— Received Waveform

Butane Sensitivity (0-100%)

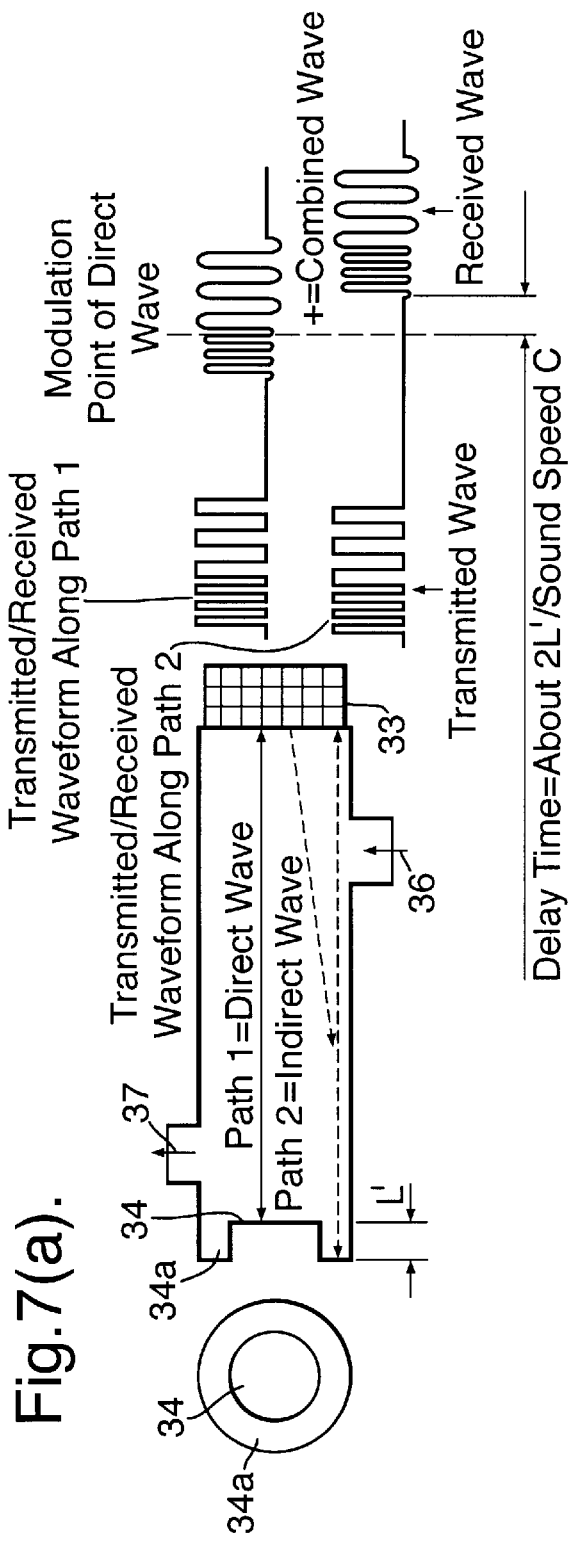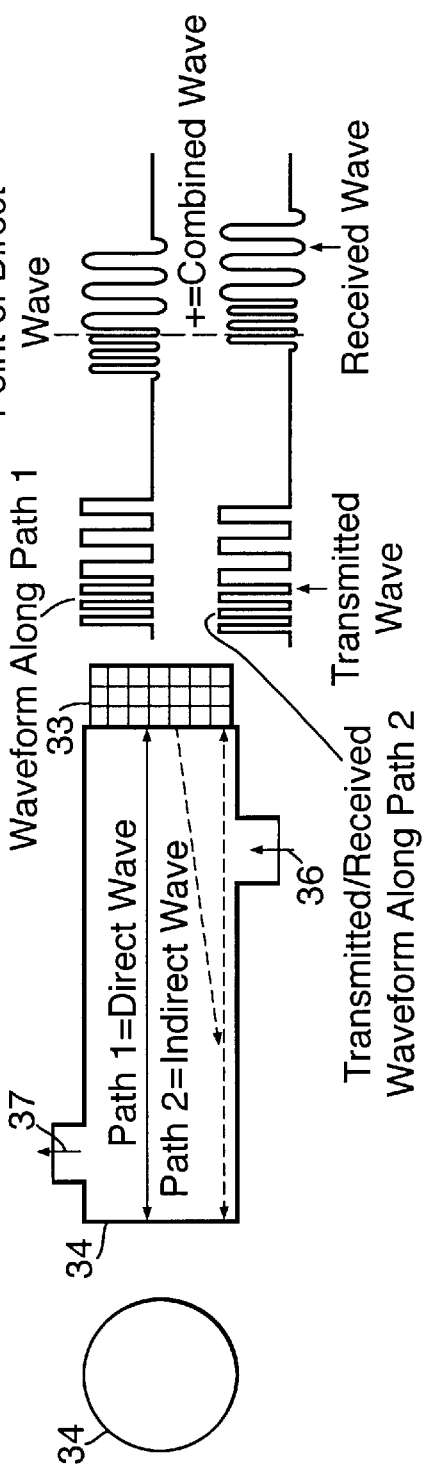
Fig.7(a).
Fig.7(b).

Transmission-Reception Changeover SW

Transmitted/Received Waveform

Waveform Input to Microcomputer= Comparator Output

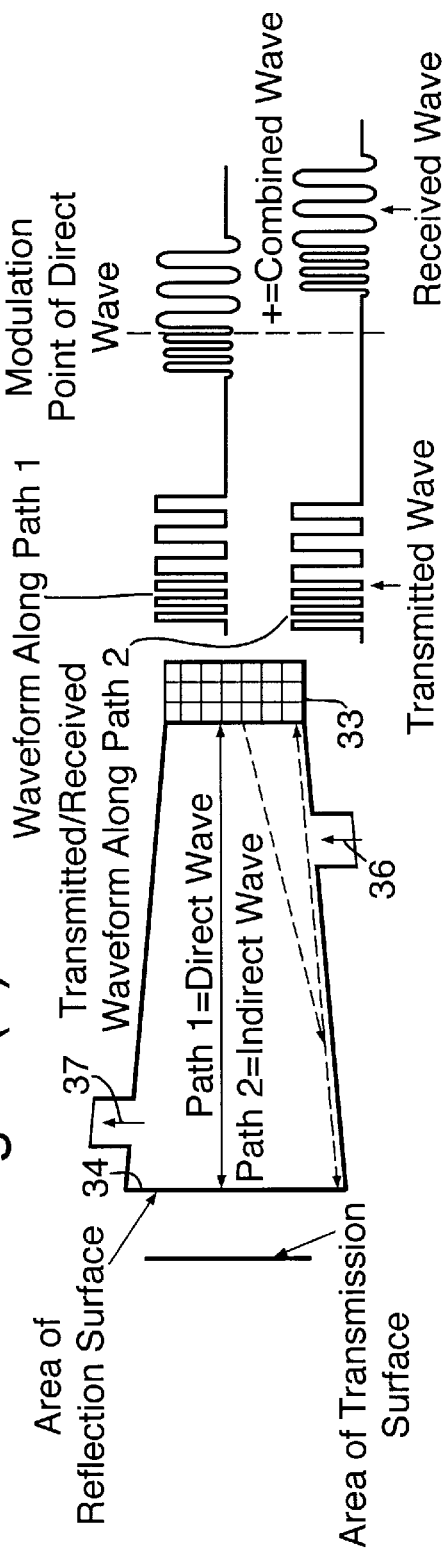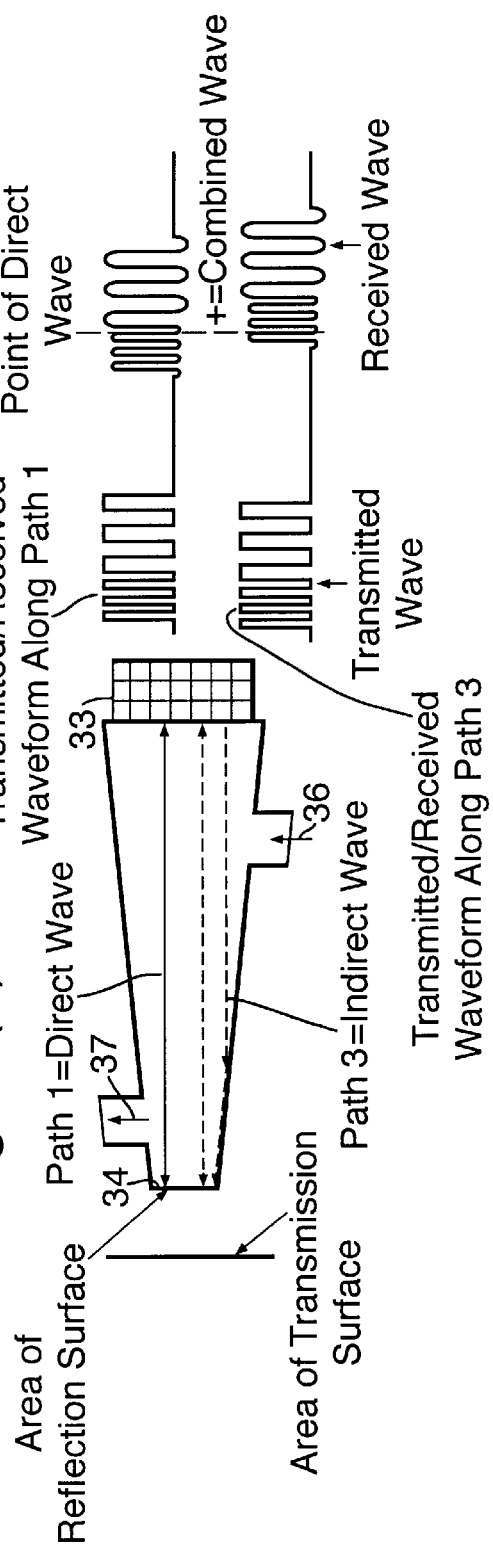

Gas Concentration Sensor 325

H₂ Charge Amount vs. Sensor output
With Distance L3 as Parameter

When Sound Speed Is Low

When Sound Speed Is High

When Sound Speed Is Low

When Sound Speed Is High

Gas Concentration Sensor 325

- ◆ Diameter of inflow path = diameter of outflow path bypass not provided
- ■ Diameter of inflow path > diameter of outflow path bypass not provided
- ▲ Diameter of inflow path > diameter of outflow path bypass provided Gas Concentration Sensor 325

GAS CONCENTRATION SENSOR

BACKGROUND OF THE INVENTION

Field of the Invention

The present invention relates to a gas concentration sensor for measuring the concentration of combustible gas, such as vaporized fuel, contained in, for example, intake air to be supplied into an intake pipe of, for example, an internal combustion engine, or for measuring the concentration of a gas component in fuel gas of a fuel cell or in exhaust gas. 2. Description of the Related Art Conventionally, a fuel supply system for supply of fuel from a fuel tank to an engine includes a first supply system which functions in the following manner. Fuel is pumped from the fuel tank by means of a fuel pump and is then sent to an injector through a fuel pipe.

The fuel supply system further includes a second supply system which functions in the following manner. Vaporized fuel generated within the fuel tank is temporarily adsorbed by a canister. Accumulated vaporized fuel is purged from the canister and is sent as purge gas to an intake pipe.

Accordingly, in addition to fuel injected from the injector, vaporized fuel, such as purge gas, is burned within a cylinder of the engine (hereinafter vaporized fuel is referred to merely as purge gas).

When, as a result of supply to the engine of purge gas in addition to injected fuel, an air-fuel ratio deviates from a theoretical value, the purification capability of a catalyst with respect to CO, HC, and NOx lowers considerably. As a result, CO, HC, and NOx contents of exhaust gas increase.

Accordingly, in order to use purge gas as a portion of main fuel for combustion, for example, at engine start-up, particularly when the catalyst is inactive, optimum control of purge gas supply through highly accurate measurement of purge gas concentration is very important.

A sensor for measuring purge gas concentration may utilize, for example, ultrasonic waves (ultrasonic sensor). Such an ultrasonic sensor has been developed, but a satisfactory ultrasonic sensor has not yet been developed.

Some ultrasonic sensors of this kind have an ultrasonic element for transmitting and receiving an ultrasonic wave having a modulation point. On the basis of the difference in time between a modulation point present in a transmitted wave and that in a received wave (i.e., on the basis of propagation time of an ultrasonic wave), purge gas concentration is determined. An ultrasonic wave which the ultrasonic element receives is actually a combined wave of a direct wave and an indirect wave. The direct wave is a component having highest sound pressure and propagating along a shortest path, and the indirect wave is a component having relatively low sound pressure and propagating along a longer path than that of the direct wave.

The indirect wave is slightly delayed in propagation with respect to the direct wave and is combined with the direct wave at a portion located in the vicinity of a modulation point of the direct wave. This causes difficulty in detecting the modulation point of the direct wave, resulting in a failure to accurately measure the propagation time of the direct wave.

Accordingly, accurate control of purge gas concentration on the basis of a measured purge gas concentration becomes considerably difficult.

In recent years, development of a fuel cell for use as a clean automobile power source has been carried out intensively. Fuel cells include a molten-carbonate fuel cell and a phosphate fuel cell. Especially, a polyelectrolyte fuel cell (PEFC) is of particular interest because of various advantages, such as easy starting and stopping, high output density, compactness, and light weight.

A polyelectrolyte fuel cell employs hydrogen as fuel. Hydrogen serving as fuel is conventionally produced by means of a reformer, in the form of a gas reformed from methanol. In order to efficiently generate power, measurement of hydrogen concentration in the reformed gas is very important. Presupposing use within combustible gas, a gas concentration sensor for measuring the hydrogen concentration desirably has a low working temperature. Japanese Patent Publication (kokoku) No. 7-31153 discloses an example of such a sensor; specifically, a sensor which employs a proton conductor film. However, the disclosed sensor involves a certain degree of heating. Also, a current-measurement-type sensor which employs NAPHYON as an electrolyte is proposed. However, this sensor has a problem in that an electrode is poisoned by CO, which is generated in a large amount during start-up, and that humidity dependency is high.

In order to detect gas concentration without involving heating and to diminish poisoning by a miscellaneous gas component or humidity dependency, a technique which utilizes the above-mentioned ultrasonic sensor used in an engine is proposed. However, when a gas component having a low molecular weight, such as hydrogen gas, is to be detected, the speed of sound becomes considerably high. As a result, the indirect wave is highly likely to overlap the direct wave, causing difficulty in detecting a modulation point. Therefore, measurement of propagation time becomes considerably difficult.

In the case of receiving such a high-speed sound wave, even a controller's switching noise, which is generated at the time of transmission of an ultrasonic wave, and reverberations overlap a received wave reflected from a reflection surface, thus disturbing wave reception.

There can also be a problem with an ultrasonic gas concentration sensor that, when the flow velocity of intake air is high, with a resultant disturbance of flow, an ultrasonic wave transmitted into the intake air suffers unstable amplitude attenuation, resulting in a failure to receive an ultrasonic wave of stable amplitude. As a result, propagation time cannot be determined accurately.

SUMMARY OF THE INVENTION

An object of the invention is to provide a gas concentration sensor capable of accurately measuring propagation time of a direct wave and capable of measuring the concentration of specific gas, such as purge gas, or the concentration of specific gas for use in a fuel cell, and to provide a gas concentration sensor capable of stably and with high accuracy measuring the concentration of a specific gas even when the gas under measurement which contains the specific gas, such as purge gas, flows at high velocity.

Accordingly, a gas concentration sensor according to the invention comprises a measurement chamber, an ultrasonic element, and gas detection means. The measurement chamber has an inflow path for allowing inflow of gas under measurement thereinto and an outflow path for allowing outflow of the gas therefrom. The ultrasonic element is disposed on one of two wall surfaces located in opposition to each other within the measurement chamber. The ultrasonic element is capable of transmitting an ultrasonic wave toward the other of the two wall surfaces and receiving an ultrasonic wave reflected from the wall surface serving as a reflection surface (the ultrasonic wave reflected is hereinafter referred to as a reflected ultrasonic wave). The gas detection means causes the ultrasonic element to transmit an ultrasonic wave and to receive the reflected wave. The gas detection means measures a propagation time between transmission of the ultrasonic wave and reception of the reflected wave. On the basis of the propagation time, the gas detection means determines the concentration of a specific gas contained in the gas under measurement. The sensor is characterized in that the measurement chamber is formed such that the distance between an edge portion of the reflection surface and the ultrasonic element is greater than that between the central portion of the reflection surface and the ultrasonic element.

As mentioned above, in the gas concentration sensor, the distance between the edge portion of the reflection surface and the ultrasonic element is greater than that between the central portion of the reflection surface and the ultrasonic element.

Accordingly, the propagation distance of an indirect wave which propagates along a side wall of the measurement chamber is lengthened, thereby preventing combination of the indirect wave and a direct wave in the vicinity of a modulation point of the direct wave.

Since a modulation point of the direct wave can be detected accurately, the propagation time can be measured accurately, enabling accurate measurement of gas concentration. On the basis of accurately measured gas concentration, gas concentration can be adjusted accurately, whereby, for example, control of air-fuel ratio can be performed favorably.

The invention also provides a gas concentration sensor comprising a measurement chamber, an ultrasonic element, and gas detection means. The measurement chamber has an inflow path for allowing inflow of gas under measurement thereinto and an outflow path for allowing outflow of the gas therefrom. The ultrasonic element is disposed on one of two wall surfaces located in opposition to each other within the measurement chamber. The ultrasonic element is capable of transmitting an ultrasonic wave toward the other of the two wall surfaces and receiving an ultrasonic wave reflected from the wall surface serving as a reflection surface. The gas detection means causes the ultrasonic element to transmit an ultrasonic wave and to receive the reflected wave. The gas detection means measures a propagation time between transmission of the ultrasonic wave and reception of the reflected wave. On the basis of the propagation time, the gas detection means determines the concentration of a specific gas contained in the gas under measurement. The sensor is characterized in that the area of the reflection surface of the measurement chamber is not less than the area of an opening surface of the ultrasonic element.

As mentioned above, the area of the reflection surface of the measurement chamber is at least equal to, preferably greater than, the area of an opening surface of the ultrasonic element (specifically, the area of a portion adapted to transmit/receive an ultrasonic wave).

Accordingly, an ultrasonic wave transmitted in parallel with the direct wave does not include a component incident on a side wall of the measurement chamber, or an indirect-wave component which propagates with a propagation time very close to that of the direct wave. Thus, since a modulation point of the direct wave can be detected accurately, the propagation time can be measured accurately, enabling accurate measurement of gas concentration. On the basis of accurately measured gas concentration, gas concentration can be adjusted accurately, whereby, for example, control of air-fuel ratio can be performed favorably.

When the area of the reflection surface is equal to that of an opening surface of the ultrasonic element, for example, an indirect wave incident on a side wall of the measurement chamber in the vicinity of the reflection surface may raise a problem. Specifically, after impinging on the side wall of the measurement chamber, this component propagates between the reflection surface and the ultrasonic element along the side wall; i.e., in parallel with the direct wave. As a result, the component propagates with a propagation time relatively close to that of the direct wave.

Therefore, it is preferable that the area of the reflection surface be greater than that of an opening surface of the ultrasonic element. In this case, after impinging on the side wall of the measurement chamber, an indirect wave propagates between the reflection surface and the ultrasonic element along the side wall. Accordingly, the propagation time of the direct wave becomes sufficiently shorter than that of the indirect wave. Thus, a modulation point of the direct wave can be detected accurately, enabling accurate measurement of propagation time.

Preferably, the distance between an edge portion of the reflection surface and the ultrasonic element is rendered greater than that between a central portion of the reflection surface and the ultrasonic element. In this case, the propagation time of the indirect wave is lengthened further, thereby further improving accuracy in detecting a modulation point of the direct wave.

Regardless of the degree of intensity of a signal, the propagation time of an ultrasonic wave can be measured accurately.

A modulation point to be introduced into the transmitted wave may be a phase changeover point associated with ordinary phase modulation. Specifically, at least one phase changeover point (for example, a point where phase is changed over from θ degrees to (θ+180) degrees) may be introduced into the waveform of an ultrasonic wave to be transmitted from the ultrasonic element. This phase changeover point also reflectingly appears in the received wave. Accordingly, for example, through measurement of the time interval between phase changeover points in a direct wave (i.e., the time interval between a phase changeover point in the transmitted wave and a phase changeover point in the received wave), propagation time can be obtained. Regardless of the degree of intensity of a signal, the propagation time of an ultrasonic wave can be measured accurately.

Preferably, the gas detection means causes the ultrasonic element to transmit an ultrasonic wave so that the ultrasonic wave is reflected from the reflection surface to thereby become a first reflected wave; the gas detection means causes the ultrasonic element to reflect the first reflected wave so that the first reflected wave is again reflected from the reflection surface; and the gas detection means measures the propagation time of a reflected wave other than the first reflected wave so as to determine the concentration of a specific gas on the basis of the propagation time.

This feature enables the gas concentration sensor to measure the propagation time of an ultrasonic wave more accurately.

For example, in the case where characteristics of a molded material of the ultrasonic element have changed due to time-course deterioration, the propagation time of the first reflected wave becomes greater than that of the first reflected wave as measured in a new sensor. If measurement of the concentration of a specific gas is based on the propagation time of the first reflected wave, gas concentration cannot be determined accurately. By contrast, a reflected wave other than the first reflected wave (for example, second reflected wave) is merely reflected from the surface of the ultrasonic element and is not affected by the internal structure of the ultrasonic element. As shown in FIG. 9, even when the sensor is deteriorated, the propagation time of, for example, the second reflected wave exhibits less variation and is less susceptible to deterioration of the sensor.

Therefore, in the gas concentration sensor preferably, the concentration of a specific gas is determined on the basis of the propagation time of the second or later reflected wave, which is less susceptible to deterioration of the sensor, instead of the propagation time of the first reflected wave, which is susceptible to deterioration of the sensor.

Thus, gas concentration can be measured accurately. On the basis of accurately measured gas concentration, gas concentration can be adjusted accurately, whereby, for example, control of air-fuel ratio can be performed favorably.

Preferably, the specific gas is vaporized fuel for use with an internal combustion engine. The gas concentration sensor is intended to measure the concentration of vaporized fuel, such as purge gas. Since fuel gas concentration can be measured accurately, an air-fuel ratio can be controlled favorably.

Meanwhile, as schematically shown in FIG. 21. components of a received waveform include not only a direct wave and an indirect wave but also a controller's switching noise, which has been generated at the time of transmission, and reverberations of an ultrasonic wave. When the speed of sound is sufficiently low as shown in FIG. 21($a$), these waveform components appear at certain intervals and thus can be identified clearly. Therefore, on the basis of the direct wave, propagation time can be measured accurately.

However, when the speed of sound is high as shown in FIG. 21($b$), the direct wave is received before a reverberation component converges sufficiently. As a result, the reverberation component and a first-half portion of the direct wave may overlap each other. Also, since there cannot be a sufficient difference in propagation time between the direct wave and the indirect wave, the indirect wave and a latter-half portion of the direct wave may overlap each other. In such a case, detection of a position in the waveform of the direct wave corresponding to a specific position in the waveform of a transmitted wave becomes difficult, causing difficulty in accurately measuring propagation time.

Accordingly the present invention provides a gas concentration sensor comprising a measurement chamber, an ultrasonic element, and gas detection means. The measurement chamber has an inflow path for allowing inflow of gas under measurement thereinto and an outflow path for allowing outflow of the gas therefrom. The ultrasonic element is disposed on one of two wall surfaces located in opposition to each other within the measurement chamber. The ultrasonic element is capable of transmitting an ultrasonic wave toward the other of the two wall surfaces and receiving an ultrasonic wave reflected from the wall surface serving as a reflection surface. The gas detection means causes the ultrasonic element to transmit an ultrasonic wave and to receive the reflected wave. The gas detection means measures a propagation time between transmission of the ultrasonic wave and reception of the reflected wave through detection of a specific position in the waveform of the ultrasonic wave. The gas detection means determines the concentration of a specific gas contained in the gas under measurement on the basis of the propagation time. The sensor is characterized in that the measurement chamber is formed such that the distance between a central portion of the reflection surface and the ultrasonic element is at least 60 mm.

The above gas concentration sensor is intended to measure the concentration of a gas component having a relatively low molecular weight. In order to effectively detect gas concentration even when the speed of sound becomes considerably high at the time of measurement of gas concentration, the invention specifies the distance between the ultrasonic element and the reflection surface.

A distance of 60 mm is obtained from experimental results, which will be described later. Through employment of this distance, the propagation time of a reflected wave can be rendered sufficiently long, whereby the reflected wave reaches the ultrasonic element after the reverberation component of a transmitted wave converges. Thus is avoided a problem that, as a result of overlapping of the reverberation component and the reflected wave, reception of the reflected wave is disturbed. Therefore, the arrival of the reflected wave can be detected accurately. This is particularly favorable in the case of measuring propagation time on the basis of the lead position of the direct wave.

Through prescription of the distance between the central portion of the reflection surface and the ultrasonic element as described above, the problem derived from overlapping of the reflected wave (direct wave) and the reverberation component can be solved. However, the problem derived from overlapping of the direct wave and the indirect wave cannot be solved. Overlapping of direct and indirect waves does not raise a problem when measurement of propagation time is based on the lead position of the direct wave. However, when measurement of propagation time is based on a modulation point of the direct wave, overlapping of direct and indirect waves prevents accurate detection of the modulation point and thus raises problem.

Specifically, when the speed of sound is sufficiently low as shown in FIG. 22($a$), waveform components appear at certain intervals; thus, a position in the waveform can be identified clearly, thereby enabling accurate measurement of propagation time. In this case, the invention provides a sufficiently long distance between the central portion of the reflection surface and the ultrasonic element, propagation time becomes greater than in the case of FIG. 21($a$).

However, in the case of a particularly high speed of sound as shown in FIG. 22($b$), the configuration according to this aspect of the invention solves the problem that a reverberation component and a first-half portion of the direct wave overlap each other, but fails to solve the problem that the indirect wave and a latter-half portion of the direct wave overlap each other, since the difference in propagation time between the direct wave and the indirect wave remains unchanged. As a result, when propagation time is to be measured on the basis of a modulation point of the direct wave, measurement of propagation time becomes difficult because of difficulty in detecting a position in the waveform of the direct wave corresponding to a specific position in the waveform of a transmitted wave.

To solve the above problem, advantageously the measurement chamber is formed such that an edge portion of the reflection surface is formed into a depression having a bottom surface parallel to the reflection surface and such that the distance between the bottom surface of the depression and the ultrasonic element is at least 18 mm greater than the distance between a central portion of the reflection surface and the ultrasonic element.

The distance between the ultrasonic element and the bottom surface of the depression formed on the reflection surface is specified so as to effectively detect gas concentration even when the speed of sound becomes considerably high at the time of measurement of gas concentration.

A distance of 18 mm is obtained from experimental results, which will be described later. Through employment of this distance, the difference in propagation distance between a direct wave and an indirect wave becomes sufficiently great, whereby the indirect wave reaches the ultrasonic element after the direct wave reaches the ultrasonic element. Thus is avoided a problem that, as a result of overlapping of the indirect wave and the direct wave, reception of a reflected wave is disturbed. Therefore, the arrival of the reflected wave can be detected accurately.

FIG. 17 shows a received waveform in the case of employment of the features as described above. As shown in FIG. 17, even when the speed of sound is high, waveform components appear at certain intervals and thus can be identified clearly. Therefore, on the basis of the direct wave, propagation time can be measured accurately.

Advantageously, the sensor is characterized in that the specific gas is hydrogen gas. This enables embodiments according to the above aspects of the invention to exhibit their effectiveness markedly. Since the molecular weight of hydrogen gas is low, at the time of gas concentration measurement, the speed of sound increases considerably with the hydrogen gas content of a mixed gas. For example, a fuel cell system employs the features of gas concentration sensor as described above in order to measure hydrogen gas concentration.

The present invention also provides a gas concentration sensor comprising a measurement chamber, an ultrasonic element, and gas concentration detection means. The measurement chamber has an inflow path for allowing inflow of gas under measurement thereinto and an outflow path for allowing outflow of the gas therefrom. The ultrasonic element is disposed on one of two wall surfaces located in opposition to each other within the measurement chamber. The ultrasonic element is capable of transmitting an ultrasonic wave toward the other of the two wall surfaces and receiving an ultrasonic wave reflected from the wall surface serving as a reflection surface (the ultrasonic wave reflected is hereinafter referred to as a reflected ultrasonic wave). The gas concentration detection means causes the ultrasonic element to transmit an ultrasonic wave and to receive the reflected wave. The gas concentration detection means measures a propagation time between transmission of the ultrasonic wave and reception of the reflected wave. On the basis of the propagation time, the gas concentration detection means determines the concentration of a specific gas contained in the gas under measurement. The sensor is characterized in that the cross-sectional area of the outflow path is smaller than the cross-sectional area of the inflow path.

As mentioned above, in the gas concentration sensor in which the ultrasonic element is disposed on only one of two wall surfaces located in opposition to each other within the measurement chamber, the cross-sectional area or diameter of the outflow path is smaller than that of the inflow path.

Accordingly, the resistance of a gas flow through the outflow path increases. Thus, even when intake air, or purge gas, flows at high velocity through piping in which the gas concentration sensor is installed, an increase in the flow velocity of intake air within the measurement chamber can be suppressed as compared with the case of a conventional gas concentration sensor in which the inflow path and the outflow path have the same diameter. While the flow velocity of intake air within the measurement chamber is low, no disturbance occurs in intake air flow within the measurement chamber, so that no amplitude attenuation occurs in an ultrasonic wave propagating within the measurement chamber.

That is, in the above gas concentration sensor, to an extent of suppression of an increase in the flow velocity of intake air within the measurement chamber, an ultrasonic wave can be detected accurately, and thus the propagation time of the ultrasonic wave can be measured accurately, as compared with the case of the conventional gas concentration sensor. Thus, gas concentration can be determined with high accuracy. Through adjustment of gas concentration on the basis of this highly accurate measurement, air-fuel ratio, for example, can be controlled favorably.

Preferably, the inflow path and the outflow path have a circular cross section. In the case where the inflow and outflow paths have a noncircular cross section, the present invention may be applied by reference to a diameter of a circle having an area equal to that of the noncircular cross section, or simply to the cross-section area of the inflow and outflow paths.

The present invention also provides a gas concentration sensor comprising a measurement chamber, a pair of ultrasonic elements, and gas concentration detection means. The measurement chamber has an inflow path for allowing inflow of gas under measurement thereinto and an outflow path for allowing outflow of the gas therefrom. The ultrasonic elements are disposed respectively on two wall surfaces located in opposition to each other within the measurement chamber and are capable of transmitting/receiving an ultrasonic wave. The gas concentration detection means causes one of the ultrasonic elements to transmit an ultrasonic wave and the other of the ultrasonic elements to receive the ultrasonic wave. The gas concentration detection means measures a propagation time between transmission of the ultrasonic wave and reception of the reflected wave. On the basis of the propagation time, the gas concentration detection means determines the concentration of a specific gas contained in the gas under measurement. The sensor is characterized in that the cross-sectional area of the outflow path is smaller than the cross-sectional area of the inflow path.

As mentioned above, in the gas concentration sensor in which the ultrasonic elements are disposed on the respective two wall surfaces located in opposition to each other within the measurement chamber, the cross-sectional area or diameter of the outflow path is smaller than that of the inflow path. This arrangement produces a similar effect as in the case of the previous gas concentration sensor. Specifically, even when intake air flows at high velocity through piping in which the gas concentration sensor is installed, to an extent of suppression of an increase in the flow velocity of intake air within the measurement chamber, an ultrasonic wave can be detected accurately, as compared with the case of a conventional gas concentration sensor in which the inflow path and the outflow path have the same diameter. Thus, since the propagation time of the ultrasonic wave can be measured accurately, gas concentration can be determined with high accuracy. Through adjustment of gas concentration on the basis of this highly accurate measurement, air-fuel ratio, for example, can be controlled favorably.

Preferably, a bypass path for connecting the inflow path and the outflow path is provided separately from the measurement chamber. Because the diameter or cross-section of the outflow path is smaller than that of the inflow path, the resistance of a gas flow through the outflow path increases. Additionally, a gas flow directed to the measurement chamber branches to the bypass path. Accordingly, the initiation of a disturbance of intake air flow within the measurement chamber can be delayed until the velocity of intake air flow within piping in which the gas concentration sensor is installed increases further.

Advantageously, the gas concentration sensor can suppress an increase in the flow velocity of intake air within the measurement chamber and thus can detect an ultrasonic wave accurately. Since the propagation time of the ultrasonic wave can be measured accurately, gas concentration can be determined with high accuracy. Through adjustment of gas concentration on the basis of this highly accurate measurement, air-fuel ratio, for example, can be controlled favorably.

Preferably, the gas detection means causes the ultrasonic element to transmit/receive an ultrasonic wave involving at least one frequency modulation and is adapted to determine the concentration of a specific gas on the basis of the propagation time obtained through utilization of the modulation point present in the ultrasonic wave. For example, when an ultrasonic wave which has undergone a single-time frequency modulation from F1 to F2 is transmitted, the frequency modulation is reflected in a received wave. Accordingly, for example, through measurement of the time interval between frequency changeover points in a direct wave (i.e., the time interval between a modulation point in a transmitted wave and a modulation point in a received wave), propagation time can be obtained. Regardless of the degree of intensity of a signal, the propagation time of an ultrasonic wave can be measured accurately.

Preferably, the gas detection means causes the ultrasonic element to transmit/receive an ultrasonic wave involving at least one antiphase component and is adapted to determine the concentration of a specific gas on the basis of the propagation time obtained through utilization of the modulation point present in the ultrasonic wave. For example, when an ultrasonic wave into which one antiphase component (180 degrees) is introduced is transmitted, no signal waveform appears at an antiphase point in a transmitted wave. This antiphase point is reflected in a received wave, or a reflected wave, in the form of a missing signal waveform. Accordingly, for example, through measurement of the time interval between antiphase points in a direct wave (i.e., the time interval between a point of missing signal waveform in the transmitted wave and a point of missing signal waveform in the received wave), propagation time can be obtained.

Preferably, the gas concentration detection means measures a propagation time between reception of an ultrasonic wave by the ultrasonic element and next reception of an ultrasonic wave by the ultrasonic element and determines the concentration of a specific gas on the basis of the propagation time. This is intended to further improve accuracy in measuring the propagation time of an ultrasonic wave.

In the case where characteristics of, for example, a molded material of the ultrasonic element have changed due to time-course deterioration, the propagation time between transmission of an ultrasonic wave and first reception of the ultrasonic wave by the ultrasonic element becomes greater than that as measured in a new sensor. Accordingly, if the concentration of a specific gas is measured on the basis of the first propagation time (i.e., a time interval between transmission of an ultrasonic wave and first reception of the ultrasonic wave by the ultrasonic element) as measured in a new sensor, the gas concentration will not be determined accurately.

By contrast, a received wave other than the first received wave (for example, an ultrasonic wave which, after being received first time by the ultrasonic element, propagates back and forth within the measurement chamber and is again received by the ultrasonic element) results from propagation through mere repetition of reflection and is not affected by the internal structure of the ultrasonic element. Thus, even when the ultrasonic element is deteriorated, the propagation time of a second or later received wave exhibits less variation and is less susceptible to deterioration of the ultrasonic element.

BRIEF DESCRIPTION OF THE DRAWINGS

FIG. 2 shows views showing a gas concentration sensor, wherein

FIG. 6 shows views showing a transmitted waveform and gas concentration sensor, wherein

FIG. 7 shows views showing transmitted/received waves, wherein

FIG. 7(a) is a view showing a transmitted/received wave in the case where a reflection surface 34 has a depression 34a formed thereon, and FIG. 7(b) is a view showing a transmitted/received wave in the case of a conventional gas concentration sensor in which the reflection surface 34 is flat;

FIG. 8 show timing charts, wherein

FIG. 11 shows views showing transmitted/received waves, wherein

FIG. 11(a) is a view showing a transmitted/received wave in the case where the area of the reflection surface 34 is greater than the area of a surface of an ultrasonic element 33 which faces the reflection surface 34, and FIG. 11(b) is a view showing a transmitted/received wave in the case where the area of the reflection surface 34 is smaller than the area of the surface of the ultrasonic element 33 which faces the reflection surface 34;

FIG. 12 shows views showing a transmitted waveform and timing chart, wherein

FIG. 16 shows views showing transmitted/received waves, wherein

FIG. 21 shows schematic views showing transmitted/received waves in the case of a distance L3 less than 60 mm combined with a distance L3' less than 18 mm, wherein

FIG. 22 shows schematic views showing transmitted/received waves in the case of a distance L3 not less than 60 mm combined with a distance L3' less than 18 mm, wherein

DESCRIPTION OF THE PREFERRED EMBODIMENTS OF THE INVENTION

First Embodiment

A gas concentration sensor according to the present embodiment utilizes an ultrasonic wave so as to measure vaporized fuel concentration.

First, the configuration of a system which employs a gas concentration sensor of the present embodiment will be described.

Figure 1:
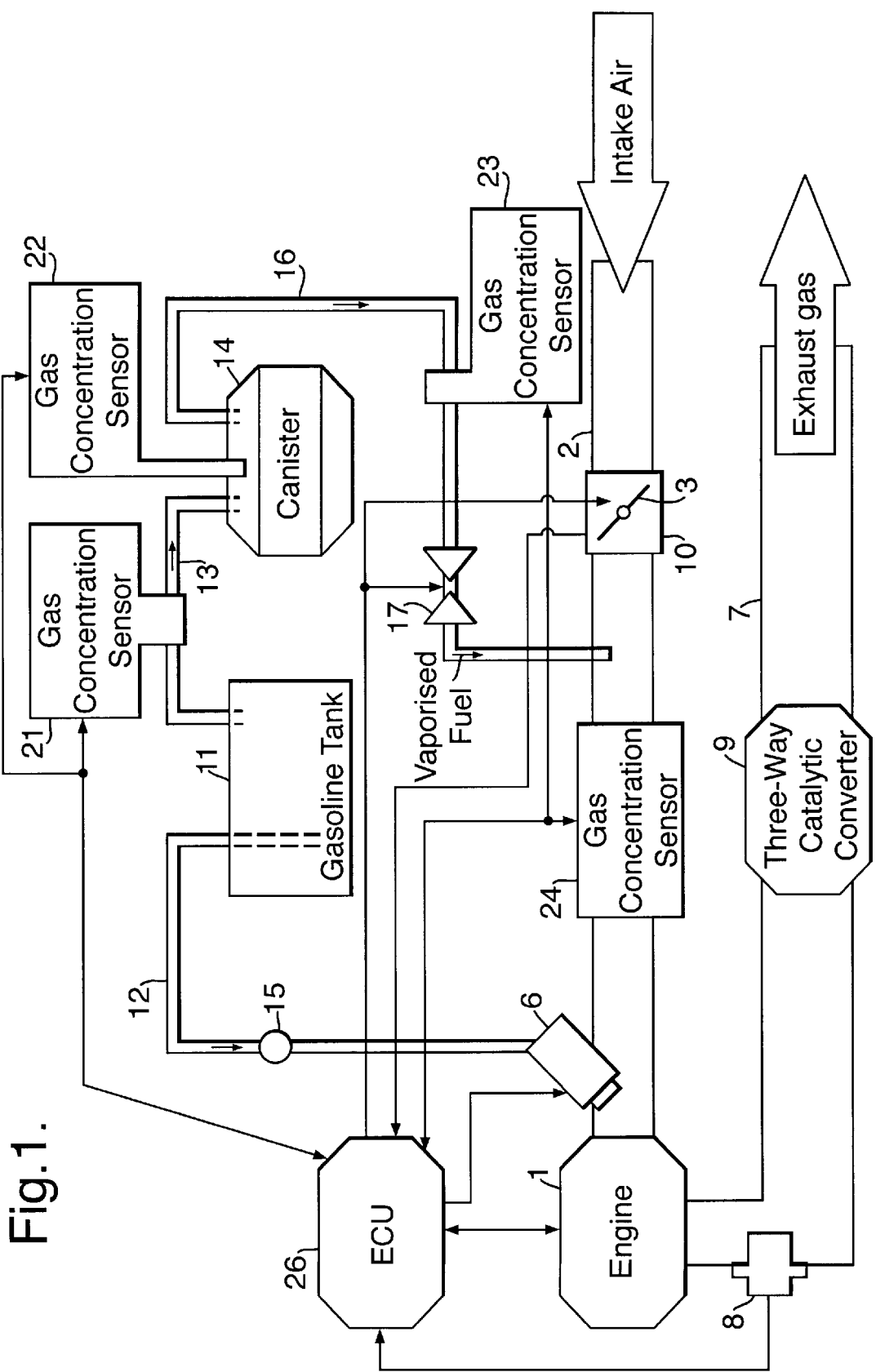
FIG. 1 is a system diagram showing an entire system which includes a controller for gas concentration sensors according to a first embodiment of the present invention.

FIG. 1 is a diagram showing a system configuration including gas concentration sensors.

As shown in FIG. 1, a throttle valve 3 for regulating intake air volume, a fourth gas concentration sensor 24 for detecting purge gas concentration, and an injector 6 for injecting fuel, from upstream side to downstream side, are disposed on an intake pipe 2 of an engine 1.

An oxygen sensor (full-range-type air-fuel ratio sensor) 8 for detecting oxygen concentration in exhaust gas and a three-way catalytic converter 9 for purifying exhaust gas, from upstream side to downstream side, are disposed on an exhaust pipe 7 of the engine 1.

A path for supplying fuel to the engine 1 includes a first supply system for supplying liquid fuel and a second supply system for supplying gas fuel.

In the first supply system, a gasoline tank 11 is connected to the injector 6 via a first supply path 12 and a fuel pump 15. Fuel is supplied, through the first supply path 12, from the gasoline tank 11 to the injector 6 by means of the fuel pump 15. Then, fuel is injected into the intake pipe 2 from the injector 6.

In the second supply system, the gasoline tank 11 is connected to a canister 14 via a second supply path 13. The canister 14 is connected, via a third supply path 16 and a purge valve 17, to a portion of the intake pipe 2 extending between the throttle valve 3 and the fourth gas concentration sensor 24.

In order to detect vaporized fuel concentration, a first gas concentration sensor 21 is disposed on the second supply path 13; a second gas concentration sensor 22 is disposed on the canister 14; and a third gas concentration sensor 23 is disposed on the third supply path 16 extending between the canister 14 and the purge valve 17. Alternatively, any one of the first through third gas concentration sensors 21 to 23 may be disposed. Vaporized fuel which is purged (ejected through evaporation) from the canister 14 is called purge gas.

Fuel which has evaporated from the gasoline tank 11 is once adsorbed by the canister 14. Outside air is introduced as appropriate into the canister 14 to thereby purge fuel. The thus-purged vaporized fuel (purge gas) undergoes flow regulation in the purge valve 17 and is then supplied into a portion of the intake pipe 2 extending between the throttle valve 3 and the fourth gas concentration sensor 24.

This system employs an electronic control unit (ECU) 26 in order to control purge gas supply and air-fuel ratio. The ECU 26 receives signals from various sensors, such as the first through fourth gas concentration sensors 21 to 24 (hereinafter generically referred to as a gas concentration sensor 25 ). the oxygen sensor 8, and an air flowmeter 10. The ECU 26 outputs control signals to various actuators, such as the purge valve 17, the throttle valve 3, and the injector 6. The ECU 26 also outputs a control signal, such as an on-off signal, to the gas concentration sensor 25.

The structure and basic principle of the gas concentration sensor 25 of the present embodiment will next be described.

First, the structure of the gas concentration sensor 25 will be described.

The gas concentration sensor 25 is an ultrasonic gas concentration sensor which generates an ultrasonic wave through utilization of a piezoelectric element. The gas concentration sensor 25 employs an ultrasonic transmitter-receiver element (element assembly) which transmits and receives an ultrasonic wave.

Figure 2A:
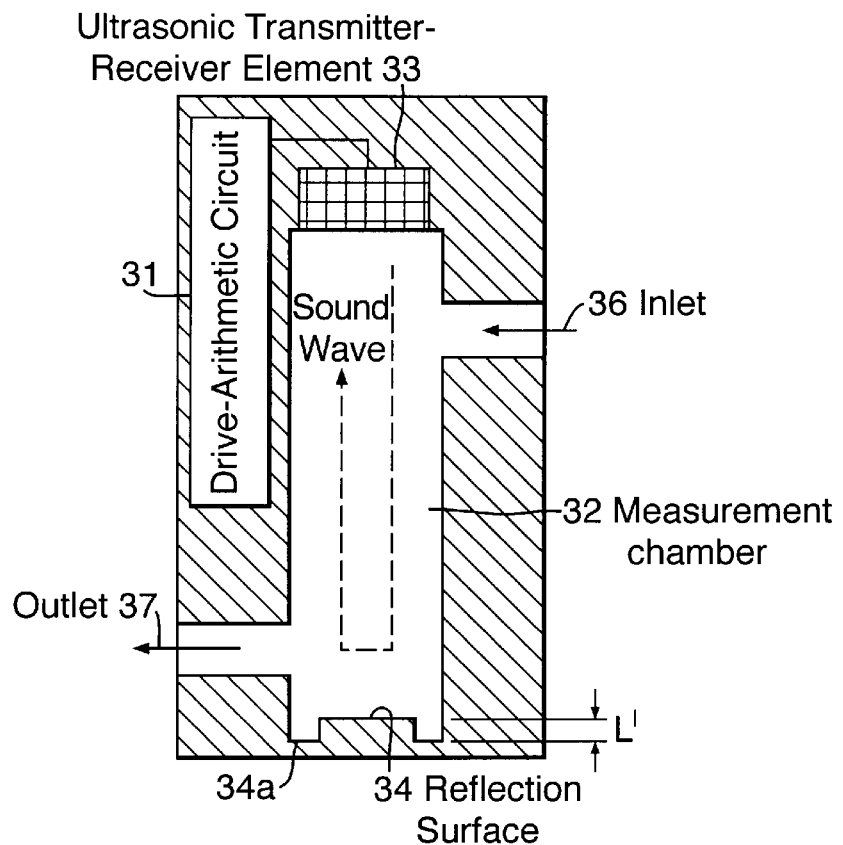
FIG. 2(a) is a view showing an entire sensor.

Specifically, as shown in FIG. 2(a), the gas concentration sensor 25 includes a drive-arithmetic circuit 31; a measurement chamber 32 into which intake air including vaporized fuel is introduced; an ultrasonic transmitter-receiver element (hereinafter referred to merely as an ultrasonic element) 33 disposed on one of two end portions located in opposition to each other within the measurement chamber 32; a reflection surface 34 adapted to reflect an ultrasonic wave within the measurement chamber 32, formed on the other end portion which faces the end portion on which the ultrasonic element 33 is disposed, and located a predetermined distance l, away from the ultrasonic element 33; an inflow hole 36 (an inlet 36 in FIG. 2(a)) for allowing inflow of intake air; and an outflow hole 37 (an outlet 37 in FIG. 2(a)) for allowing outflow of intake air. A depression 34a is formed on an edge portion of the reflection surface 34 which is in contact with a side wall of the measurement chamber 32. The bottom surface of the depression 34a is substantially in parallel with the reflection surface 34. The distance between the ultrasonic element 33 and the bottom surface of the depression 34a is L' greater than the distance between the ultrasonic element 33 and a central portion of the reflection surface 34.

Figure 2B:
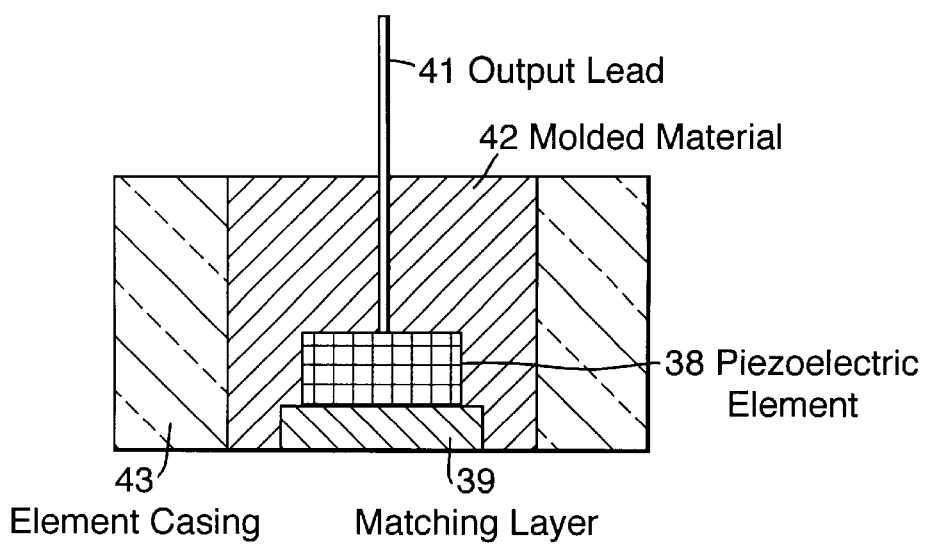
FIG. 2(b) is a view showing an ultrasonic transmitter-receiver element.

As shown in FIG. 2(b), the ultrasonic clement 33 includes a piezoelectric element 38; a matching layer 39 affixed to an end face of the piezoelectric element 38 so as to be exposed to the measurement chamber 32; an output lead 41 extending outward from the piezoelectric element 38 in order to output a sensor output from the piezoelectric element 38; and an element casing 43 in which the piezoelectric clement 38, the matching layer 39, and an end portion of the output lead 41 connected to the piezoelectric element 38 are fixed by means of a molded material 42. An end face of the matching layer 39 that faces the measurement chamber 32 is substantially flush with an end face of the element casing 41 that faces the measurement chamber 32. An oil resistant, heat resistant, thin resin film is affixed to the end faces of the matching layer 39 and element casing 43 that face the measurement chamber 32.

Next, the configuration of the drive-arithmetic circuit 31 of the gas concentration sensor 25, which corresponds to the gas detection means of the present invention, will be described.

Figure 3:
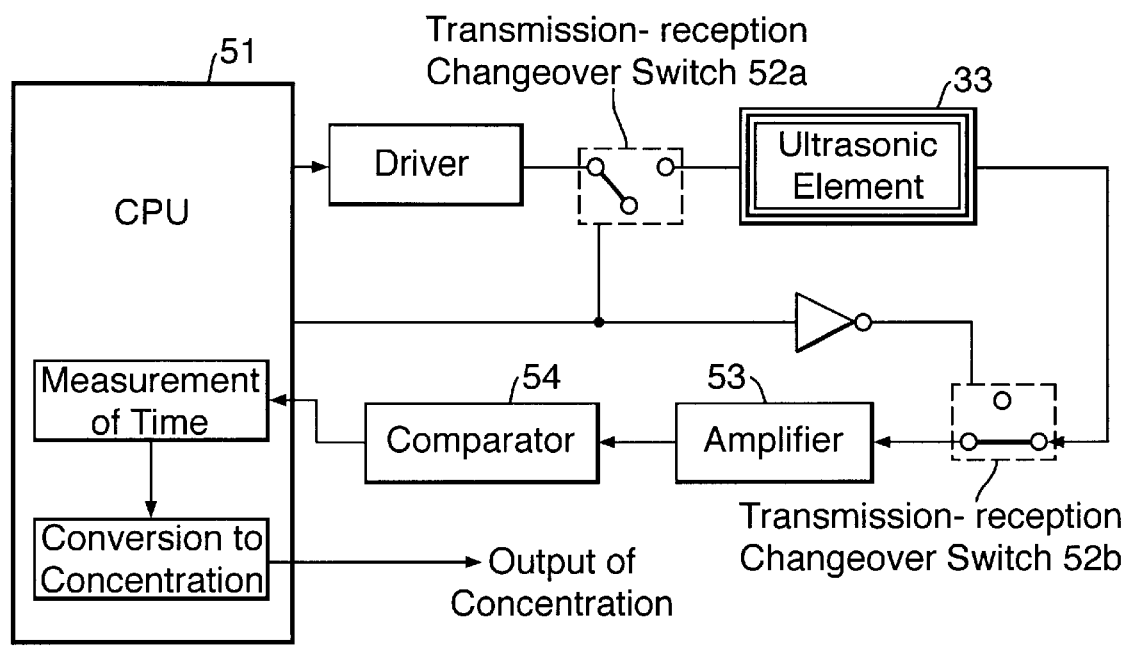
FIG. 3 is block diagram showing the electrical configuration of a gas concentration sensor.

As shown in a block diagram of FIG. 3, a CPU (microcomputer) 51 is used to drive the gas concentration sensor 25 and to perform arithmetic operations. Transmission and reception of an ultrasonic wave is changed over to each other by means of transmission-reception changeover switches 52a and 52b.

At the time of transmission, voltage is applied to the ultrasonic element 33 by use of a driver, to thereby transmit an ultrasonic wave. At the time of reception, an waveform received by the ultrasonic element 33 undergoes predetermined amplification at an amplifier 53 and is then shape-corrected at a comparator 54. The thus-shape-corrected signal is input to the CPU 51. The CPU 51 measures propagation time by use of a timer and converts the measured propagation time into concentration through reference to a map. The CPU 51 outputs the obtained concentration data to an unillustrated display unit.

Next, the basic principle of the gas concentration sensor 25 will be described.

For convenience of explanation, in FIG. 4, a transmitter 25b and a receiver 25a are shown as separate elements. However, in the present embodiment, the same element performs transmission and reception.

Figure 4A:
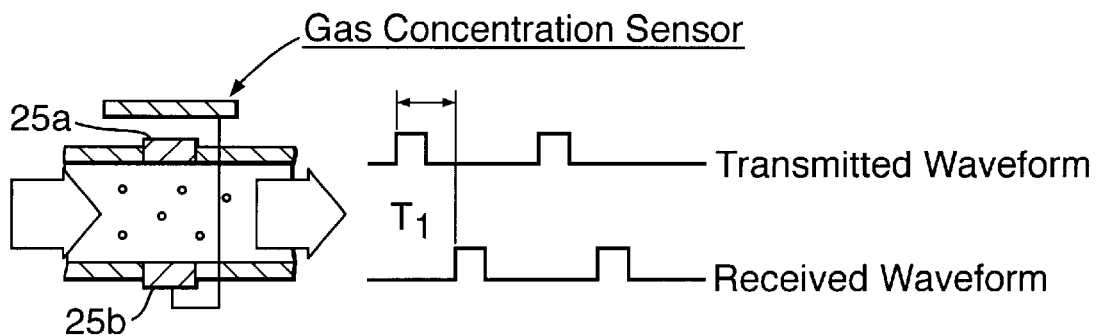
FIGS. 4(a) and 4(b) show views for explaining the basic principle of a gas concentration sensor.
Figure 4B:
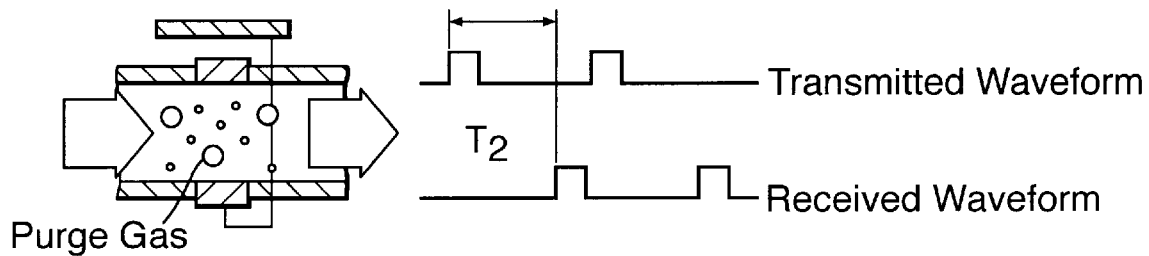

As shown in FIG. 4, in concentration measurement by use of the gas concentration sensor 25, an ultrasonic wave is transmitted from the transmitter 25b, and the ultrasonic wave is received by means of the receiver 25a. In this case, there is a time lag in propagation between a transmitted waveform and a received waveform according to, for example, purge gas concentration in intake air. For example, as shown in FIG. 4(a), when purge gas concentration is low, a propagation time T1, which is a time lag between the transmitted wave form and the received waveform, is short. By contrast, as shown in FIG. 4(b), when purge gas concentration is high, a propagation time T2 is long. Accordingly, through obtainment of a sensor output corresponding to propagation time, gas concentration can be determined.

Figure 5:
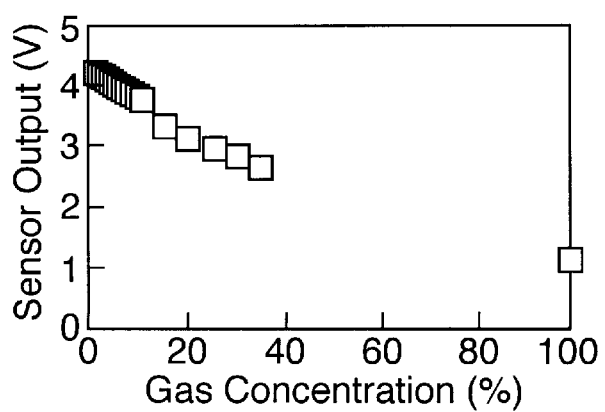
FIG. 5 is a graph showing the relationship between sensor output and butane concentration.

For example, measurement of gas concentration of butane, which is a main component of vaporized fuel, has revealed that a sensor output is substantially proportional to butane gas concentration as shown in FIG. 5. Accordingly, through obtainment of a sensor output, purge gas concentration can be determined from the obtained sensor output.

Next will be described an actual method of measuring vaporized fuel (purge gas) concentration by means of the gas concentration sensor 25 which operates according to the above-mentioned basic principle.

First, an arithmetic expression example for calculating gas concentration from propagation time of an ultrasonic wave will be described.

Figure 6A:
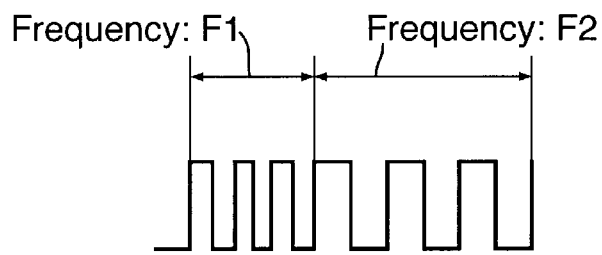
FIG. 6(a) is a view showing the transmitted waveform involving one frequency modulation.

In the present embodiment, as shown in FIG. 6(a), an ultrasonic wave which includes two kinds of frequency components, F1 and F2, is transmitted. That is, transmission frequency is modulated from F1 to F2.

In this case, since a received wave reflects the frequency modulation, arrival time is when a modulation point appears in the received wave. Through measurement of a time interval between frequency changeover points (for example, between a modulation point of the transmitted wave and that of the received wave), propagation time is obtained.

After propagation time is measured, the speed of sound C of an ultrasonic wave, which represents gas concentration, is calculated by use of expression (1) shown below.

Figure 6B:
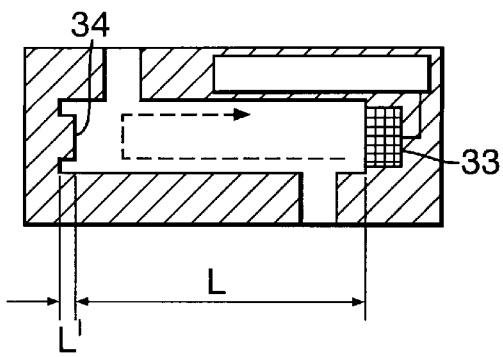
FIG. 6(b) is a view for explaining a distance between an ultrasonic element and a reflection surface.

As shown in FIG. 6(b), a distance L between the outer surface of the ultrasonic element 33 (surface of a thin resin film affixed to the matching layer 39) and the reflection surface 34 is known. A propagation time T, which is a time interval required to propagate back and forth over the distance L, is measured. The known distance L and the measured propagation time T are substituted into the following expression (1) to thereby calculate the speed of sound C.

$$i\ C=2L(\text{distance to propagate back and forth between element surface and reflection surface})/T(\text{propagation time}) \qquad (1)$$

When vaporized fuel concentration is to be determined by use of, for example, butane gas concentration Xk (butane is a main component of vaporized fuel), the speed of sound C obtained by use of the above expression (1) is converted to vaporized fuel concentration (i.e., butane gas concentration Xk) by use of the following expression (2).

$$C = \sqrt{\frac{RT_g \cdot \sum C_{pn} X_n}{\sum C_{vn} \cdot \sum M_n X_n}} \quad (2)$$

In expression (2), R represents a gas constant; $T_g$ represents the temperature of intake air which contains vaporized fuel; $C_{pn}$ represents the isopiestic specific heat of an nth component gas contained in intake air; $C_{vn}$ represents the isovolumic specific heat of the nth component gas; $M_n$ represents the molecular weight of the nth component gas; and $X_n$ represents the mixing ratio of the nth component gas (i.e., the concentration of the nth component gas).

For example, through presumption of types and mixing ratios with respect to gas components other than butane contained in intake air in which an ultrasonic wave propagates, the butane gas concentration Xk can be determined on the basis of the propagation time T and the intake air temperature $T_g$ by use of the above expression (2). In this case, if the intake air temperature $T_g$ is constant, the butane gas concentration Xk and a sensor output corresponding to the speed of sound C hold a proportional relationship as shown in FIG. 5. This proportional relationship may be used in the form of a map. Through reference to a map as shown in FIG. 5 with respect to a sensor output (voltage) corresponding to the speed of sound C, gas concentration can be obtained.

Since the depression 34a is formed at an edge portion of the reflection surface 34, a modulation point can be identified easily.

FIG. 7 shows a difference in a reflected wave received by the ultrasonic element 33 between a case where the reflection surface 34 has the depression 34a formed thereon and a case where the reflection surface 34 is flat.

In FIG. 7, among components of an ultrasonic wave transmitted from the ultrasonic element 33, a component propagating along a path 1 has the highest sound pressure (sensitivity) and propagates with a short propagation time (i.e., the component propagates along the shortest path between the ultrasonic element and the reflection surface and is hereinafter referred to as a direct wave); and among components of the ultrasonic wave transmitted from the ultrasonic element 33, a component propagating along a path 2 has a relatively low sound pressure (sensitivity) and propagates with a long propagation time (i.e., the component propagates along an indirect path and is hereinafter referred to as an indirect wave).

According to characteristics of a sound wave, when a sound wave propagating in a substance impinges obliquely on another substance having a different acoustic impedance, there is a component of the sound wave which propagates along the boundary surface between the substances (boundary surface between gas and solid; in this case, a side wall of the measurement chamber 32), as conventionally known. The path 2 represents a path along which such a component propagates.

An object of measurement is the propagation time of a component which propagates over a distance of 2 L; i.e., the propagation time of a direct wave.

In the case of a conventional gas concentration sensor (FIG. 7(b)) having a plane reflection surface, an indirect wave which propagates slightly behind a direct wave (particularly, a component which, after being transmitted from the ultrasonic element 33, follows the steps of: impinging on a side wall of the measurement chamber 32 in the vicinity of the reflection surface 34; propagating along the side wall to the reflection surface 34; being reflected from the reflection surface 34; and propagating again along the side wall of the measurement chamber 32 to thereby reach the ultrasonic element 33) is combined with the direct wave in the vicinity of a modulation point of the direct wave. Therefore, detection of the modulation point of the direct wave becomes difficult, resulting in a failure to accurately measure the propagation time T.

In the case of the reflection surface 34 having the depression 34a formed thereon (FIG. 7(a)), an indirect wave propagates more behind a direct wave as compared to the case of the plane reflection surface 34. In this case, the indirect wave is reflected from the bottom surface of the depression 34a, which is more distant from the ultrasonic element 33 than is a central portion of the reflection surface 34. Accordingly, the indirect wave propagates over a distance which is 2 L' greater than in the case of the plane reflection surface 34, thereby avoiding combination of the indirect wave and the direct wave in the vicinity of a modulation point of the direct wave. Thus, the modulation point of the direct wave can be detected accurately, so that the propagation time T can be measured accurately. Since the speed of sound C can be obtained accurately by means of the above-mentioned expression (1), vaporized fuel concentration can be determined highly accurately.

In actuality, a reflected wave is detected in the following manner in order to further improve measurement accuracy.

Figure 8A:
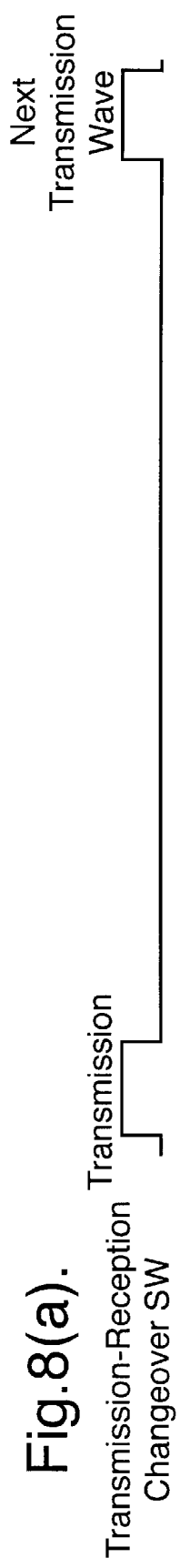
FIG. 8(a) is a timing chart showing a signal emitted from a transmission-reception changeover switch.
Figure 8B:
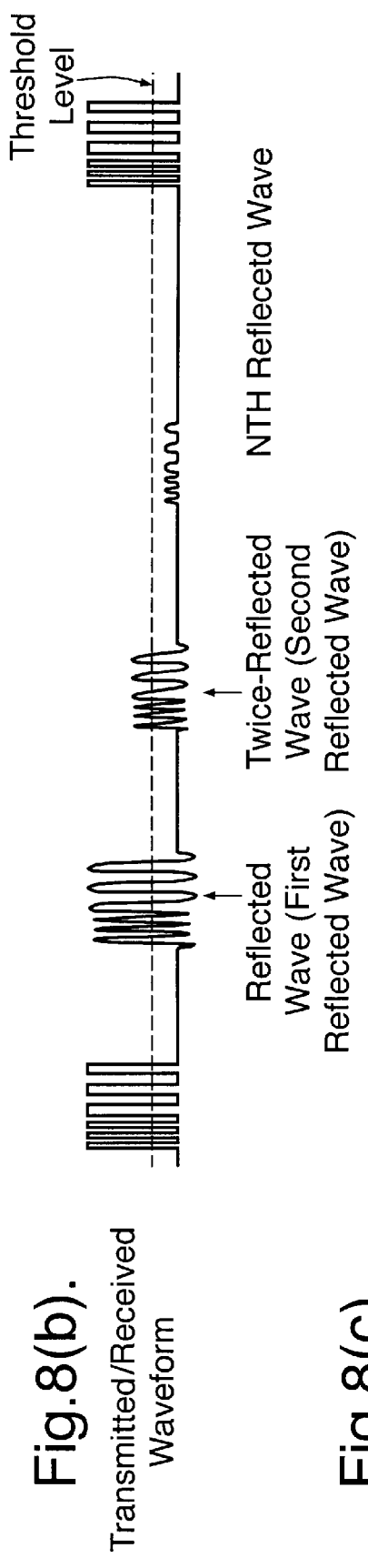
FIG. 8(b) is a timing chart showing a transmitted/received waveform.

FIG. 8(b) shows a waveform transmitted from and received by the ultrasonic clement 33. In order to describe a method of detecting a direct wave, only the waveform of the direct wave is shown in FIG. 8(b).

When the ultrasonic element 33 transmits a frequency-modulated wave, the transmitted wave is reflected from the reflection surface 34. The reflected wave is detected as a first reflected wave by the ultrasonic element 33. The first reflected wave is reflected from the surface of the ultrasonic element 33 and is reflected again from the reflection surface 34. The reflected first reflected wave is detected again as a second reflected wave by the ultrasonic element 33. Subsequently, similar reflection is repeated. As a propagation distance increases, a reflected wave attenuates gradually.

Subsequently, upon elapse of a predetermined time after transmission of the first wave, in order to transmit the next wave, the transmission-reception changeover switches 52a and 52b are changed over. As a result, as shown in FIG. 8(a), the next wave is transmitted, followed by repetition of similar processing.

Figure 8C:
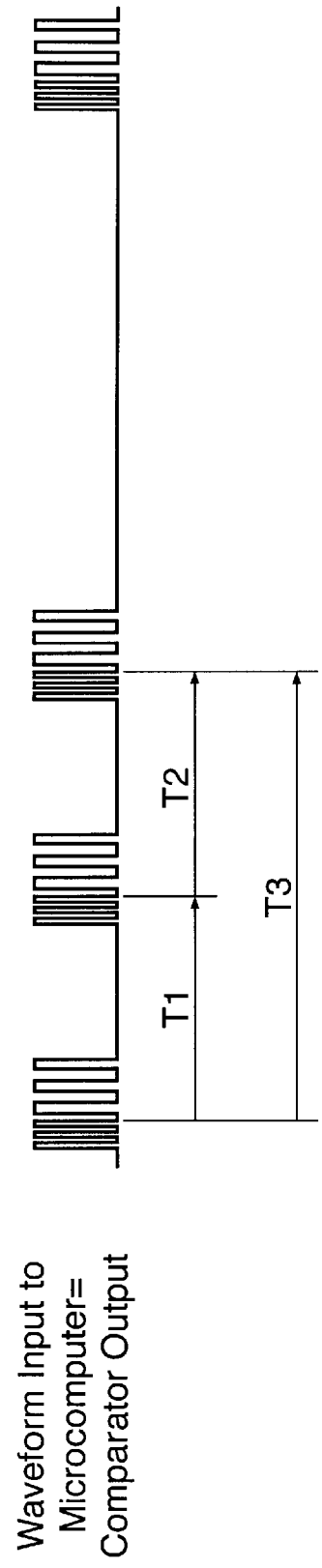
FIG. 8(c) is a timing chart showing a comparator output.

A waveform input to the microcomputer (i.e., an output from the comparator) is as shown in FIG. 8(c). A time interval between frequency modulation points is measured. That is, a received wave is compared with a predetermined threshold level by the comparator to thereby be converted to a digital signal (a binary signal of high or low level). The digital signal is input to the microcomputer. The microcomputer measures the rise time and fall time of the digital signal by means of an internal timer so as to identify a modulation point, thereby obtaining a time interval between modulation points.

Specifically, first, a first arrival time (first propagation time) T1 between a modulation point of the transmitted wave and a modulation point of the first reflected wave is measured. Also, a second arrival time T3 between the modulation point of the transmitted wave and a modulation point of the second reflected wave is measured. The first arrival time T1 is subtracted from the second arrival time T3 to thereby obtain the propagation time of the second reflected wave (second propagation time T2).

Accordingly, in the present embodiment, the thus-obtained propagation time T2 is used to determine gas concentration. the reason for using T2 is described below.

The first propagation time T1 varies due to, for example, time-course deterioration of the molded material 42 of the ultrasonic element 33. When the molded material 42 hardens or absorbs water to become heavier, the inertia of the piezoelectric element 38 varies. Conceivably, this inertia change not only affects the amplitude of the received waveform (sensitivity) but also causes a shift of a modulation point.

Figure 9:
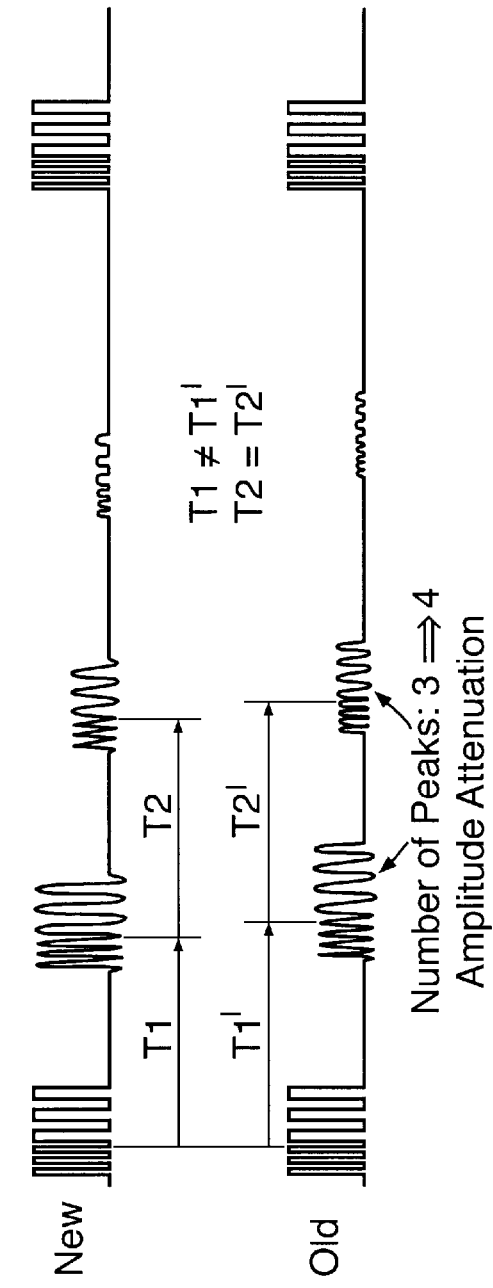
FIG. 9 is a timing chart showing a transmitted/received waveform of an ultrasonic wave in each of new and deteriorated sensors.

Specifically, for example, as seen from FIG. 9 which compares waveforms between a new sensor and an old sensor suffering time-course deterioration, the first reflected wave of the old sensor shows an increase in the number of peaks and amplitude attenuation. As a result, a first propagation time T1' as determined by the old sensor becomes greater than a first propagation time T1 as determined by the new sensor. However, since the first reflected wave is reflected similarly from the surface of the ultrasonic element 33 and is then reflected from the reflection surface 34 to thereby become the second reflected wave, the second reflected wave is free from influence of time-course deterioration. Accordingly, a second propagation time T2 as determined by the new sensor becomes equal to a second propagation time T2' as determined by the old sensor.

Accordingly, through use of the second propagation time in calculating the speed of sound C, the speed of sound C can always be calculated properly without being susceptible to time-course deterioration.

Even when time-course deterioration is involved, since a modulation point of the first reflected wave and that of the second reflected wave are both shifted, use of the second propagation time cancels a shift of a modulation point derived from a time-course variation. Thus, even when a time-course variation is involved, propagation time can be measured properly.

In the present embodiment, the speed of sound C is calculated by use of the above-mentioned second propagation time to thereby obtain a sensor output corresponding to the calculated speed of sound C. A predetermined map as shown in FIG. 5 is referred to with respect to the obtained sensor output to thereby determine gas concentration.

As described above, in the gas concentration sensor 25 of the present embodiment, the depression 34a is formed at an edge portion of the reflection surface 34, whereby a modulation point of the direct wave can be detected accurately as compared to the case of the plane reflection surface 34. Therefore, the propagation time T can be determined accurately.

Since the second propagation time is used in calculating the speed of sound C, the speed of sound C can always be calculated properly without being susceptible to time-course deterioration.

The above embodiment is described while mentioning subtraction of the first arrival time T1 from the second arrival time T3 so as to obtain the propagation time of the second reflected wave (second propagation time T2). However, the nth arrival time $T_{n+1}$ may be subtracted from the (n+1)th arrival time $T_{n+2}$ so as to obtain the propagation time of the (n+1)th reflected wave ((n+1)th propagation time $T_{n+1}$) (n is an integer of 2 or greater). however, as a propagation distance increases, a reflected wave attenuates gradually. As a result, measurement accuracy decreases with the number of reflections.

Alternatively, a time interval between a certain modulation point and the next modulation point (for example, a modulation point of the first reflected wave and a modulation point of the second reflected wave) may be directly measured as a propagation time. Performance of measurement is similar to that in the case of the above-described embodiment.

A portion of a waveform at a modulation point may suffer poor reproducibility at a certain threshold level setting of the comparator 54. Therefore, a modulation point may be used merely as an index point. A peak of the waveform located appropriately away from the modulation point may be used as an object of detection.

In the above-described embodiment, the frequency of the transmitted wave is modulated once from F1 to F2. However, the transmitted wave may involve two or more frequency modulations.

In the above-described embodiment, an edge portion of the reflection surface 34 is formed into the depression 34a having a bottom surface substantially parallel to the reflection surface 34. However, the present invention is not limited thereto. The reflection surface 34 may assumes any profile so long as the distance between the ultrasonic element 33 and an edge portion of the reflection surface 34 is greater than that between the ultrasonic element 33 and a central portion of the reflection surface 34. Needless to say, an effect yielded in the above embodiment is also yielded similarly.

Figure 10:
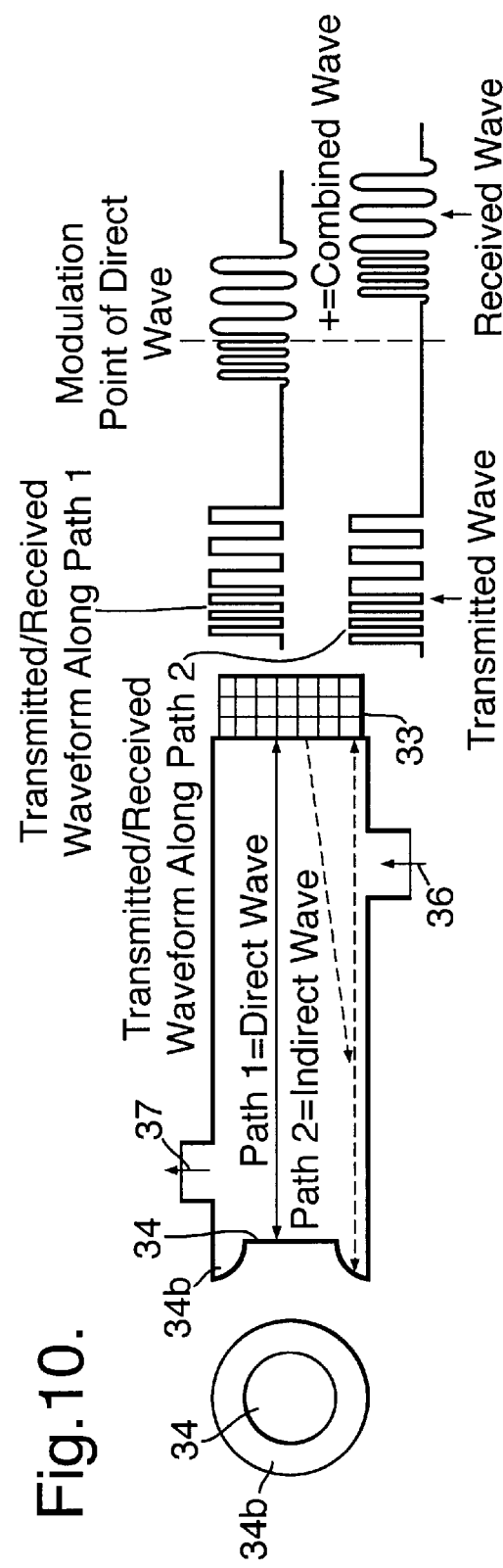
FIG. 10 is a view showing a transmitted/received wave in the case where the reflection surface 34 has a modified depression 34b formed thereon.

FIG. 10 shows an example of the above case. An edge portion of the reflection surface 34 is formed into a depression 34b profiled differently from the depression 34a shown in FIG. 7(a).

As shown in FIG. 10, the depression 34b a curved surface which extends from an edge portion of the reflection surface 34 to a side wall of the measurement chamber 32 such that the distance between the curved surface and the ultrasonic element 33 becomes longest at the contact position between the curved surface and the side wall. As in the case of the above-described embodiment, an indirect wave propagating along a path 2 is sufficiently delayed with respect to a direct wave propagating along a path 1. Thus, a modulation point of the direct wave can be detected accurately, whereby the propagation time T can be determined accurately.

Second Embodiment

Next, a second embodiment will be described.

Description of features similar to those of the above-described first embodiment will be omitted or simplified.

As shown in FIG. 11(a), the present embodiment is characterized in that the area of the reflection surface 34 is greater than that of an opening surface of the ultrasonic element 33 (specifically, the area of a portion for transmitting/receiving an ultrasonic wave).

As shown in FIG. 11(b), in the case where the area of the reflection surface 34 is smaller than that of the opening surface of the ultrasonic element 33, ultrasonic-wave components transmitted in parallel with a direct wave propagating along a path 1 include an indirect wave which impinges on a side wall of the measurement chamber 32 in the vicinity of the reflection surface 34. The indirect wave includes a component which, after impinging on the side wall of the measurement chamber 32, propagates along the side wall to the reflection surface 34 and is reflected from the reflection surface 34 and then propagates to the ultrasonic element 33 along a path parallel to the direct wave (i.e., a component which propagates along a path 3). The propagation time of such a component is very close to that of the direct wave. Accordingly, this indirect-wave component is combined with the direct wave in the vicinity of a modulation point of the direct wave, causing difficulty in detecting the modulation point. As a result, the propagation time T cannot be determined accurately.

In the case where the area of the reflection surface 34 is equal to that of the opening surface of the ultrasonic element 33, ultrasonic-wave components transmitted in parallel with the direct wave do not include a component which impinges on the side wall of the measurement chamber 32; i.e., a component, such as the indirect wave propagating along the path 3, which propagates with a propagation time very close to that of the direct wave. Thus, a modulation point of the direct wave can be detected accurately, whereby the propagation time T can be determined accurately.

However, in this case, for example, an indirect wave which impinges on the side wall of the measurement chamber 32 in the vicinity of the reflection surface 34 may be combined with the direct wave in the vicinity of a modulation point of the direct wave. After impinging on the side wall of the measurement chamber 32 in the vicinity of the reflection surface 34, this indirect wave propagates to the reflection surface 34 along the side wall. Then, after being reflected from the reflection surface 34, the indirect wave propagates toward the ultrasonic element 33 along a path parallel to the direct wave. As a result, the indirect wave propagates with a propagation time which is relatively close to that of the direct wave.

Accordingly, more preferably, the area of the reflection surface 34 may be rendered greater than that of the opening surface of the ultrasonic element 33. In this case, as shown in FIG. 11(*a*), an indirect wave which impinges on the side wall of the measurement chamber 32 propagates along a path 2. Specifically, the indirect wave impinges on the side wall of the measurement chamber 32 and propagates to the reflection surface 34 along the side wall. After being reflected from the reflection surface 34, the indirect wave propagates along the side wall until arrival at the ultrasonic element 33. Thus, the propagation time of the direct wave becomes sufficiently short as compared to that of such an indirect wave, so that a modulation point of the direct wave can be detected more accurately to thereby determine the propagation time T accurately.

In this case, if an edge portion of the reflection surface 34 is formed into the depression 34*a* (34*b*) as in the case of the first embodiment, the propagation time of the indirect wave is still lengthened. Thus, a modulation point of the direct wave can be detected more accurately.

Third Embodiment

Next, a third embodiment will be described.

Description of features similar to those of the above-described first embodiment will be omitted or simplified.

The present embodiment is intended to measure the concentration of a gas component having a low molecular weight, such as hydrogen gas, by means of an ultrasonic sensor; i.e., to effectively detect such a gas concentration even when the speed of sound becomes considerably high during measurement of gas concentration. Thus, the present embodiment is characterized by specifying a distance equivalent to the distance L between the reflection surface 34 and the outer surface of the ultrasonic element 33 (FIGS. 6 and 7) and a distance equivalent to the distance L' between the outer surface of the ultrasonic element 33 and the bottom surface of the depression 34*a* formed on the reflection surface 34.

First, the structure of a gas concentration sensor 325 employed in the present embodiment will be described.

Figure 13:
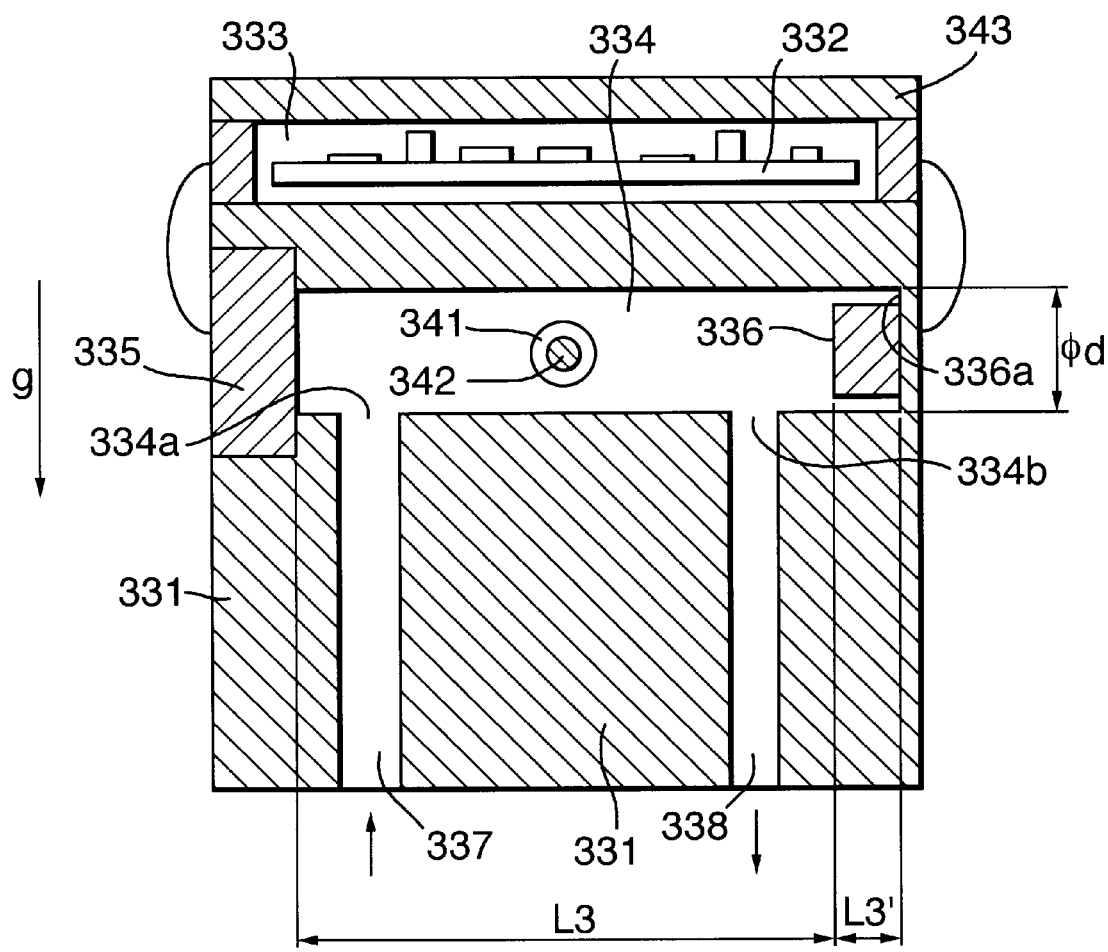
FIG. 13 is a sectional view showing a gas concentration sensor according to a third embodiment of the present invention.

The gas concentration sensor 325 employs an ultrasonic transmitter-receiver element (element assembly) similar to that employed in the first embodiment. Specifically, the gas concentration sensor 325 assumes a structure as shown in FIG. 13.

A sensor casing 331 is a body of the gas concentration sensor 325 and assumes an integral structure formed of metal or resin. The sensor casing 331 includes a circuit-board enclosing chamber 333 in which a driver-arithmetic circuit 332 is disposed; a measurement chamber 334 which is formed into a cylindrical shape having a diameter (Φ) of 12 mm and which has an inflow hole 334*a* and an outflow hole 334*b* formed in a side wall extending in the longitudinal direction thereof, the inflow hole 334*a* allowing hydrogen-gas-containing intake air to flow thereinto, the outflow hole 334*b* allowing the intake air to flow out therefrom; an ultrasonic transmitter-receiver element (hereinafter referred to merely as an ultrasonic element) 335 disposed on one of two end wall surfaces which face each other with respect to the longitudinal direction of the measurement chamber 334 within the measurement chamber 334; a reflection surface 336 implemented by the other end wall surface which faces the end wall surface on which the ultrasonic element 335 is disposed, located a predetermined distance L3 away from the ultrasonic element 335, and adapted to reflect an ultrasonic wave transmitted from the ultrasonic element 335; an inflow path 337 connected to the inflow hole 334*a* and adapted to allow the intake air to flow into the measurement chamber 334 from outside the sensor casing; and an outflow path 338 connected to the outflow hole 334*b* and adapted to allow the intake air to flow out from the measurement chamber 334 to the exterior of the sensor casing 331. When the gas concentration sensor 325 is installed actually, the longitudinal direction of the measurement chamber 334 becomes substantially parallel to the horizontal direction, and the inflow hole 334*a* and the outflow hole 334*b* are located at the lower side of the measurement chamber 334 (i.e., the gas concentration sensor 325 is installed such that the arrow g of FIG. 13 points substantially downward). An edge portion of the reflection surface 336 which is in contact with the side wall of the measurement chamber 334 is formed into a depression 336*a* having a bottom surface which is substantially parallel to the reflection surface 336. An indirect-wave component of an ultrasonic wave transmitted from the ultrasonic element 335 is reflected from the bottom surface of the depression 336*a*.

In order to effectively detect gas concentration even when the concentration of a gas component having a low molecular weight, such as hydrogen gas; i.e., even when the speed of sound becomes considerably high during measurement of gas concentration, the present embodiment specifies dimensions in the following manner: the distance L3 between the outer surface of the ultrasonic element 335 and a central portion of the reflection surface 336 is at least 60 mm; and a distance L3' between the bottom surface of the depression 336*a* formed on the reflection surface 336 and the outer surface of the ultrasonic element 335 is at least 18 mm (i.e., the distance between the bottom surface of the depression 336*a* and the ultrasonic element 335 is at least 18 mm greater than the distance between the central portion of the reflection surface 336 and the ultrasonic element 335).

A depression 341 is formed on a portion of the side wall located within the measurement chamber 334 between the inflow hole 334*a* and the outflow hole 334*b*. The depression 341 assumes the shape of a circle having a diameter of 9 mm. A temperature-sensing element 342, such as a thermistor, for measuring the temperature of intake air within the measurement chamber 334 is disposed at a central portion of the depression 341. Since the temperature-sensing element 342 is disposed within the depression 341 formed on the internal side wall of the measurement chamber 334, the temperature-sensing element 342 does not hinder propagation of an ultrasonic wave within the measurement chamber 334, thereby causing no error in measurement of the propagation time T of an ultrasonic wave.

After the drive-arithmetic circuit 332 is installed within the circuit-board enclosing chamber 333, the chamber 333 is sealed by means of a circuit cover 343.

Next, the configuration of the drive-arithmetic circuit 332 will be described.

Figure 14:
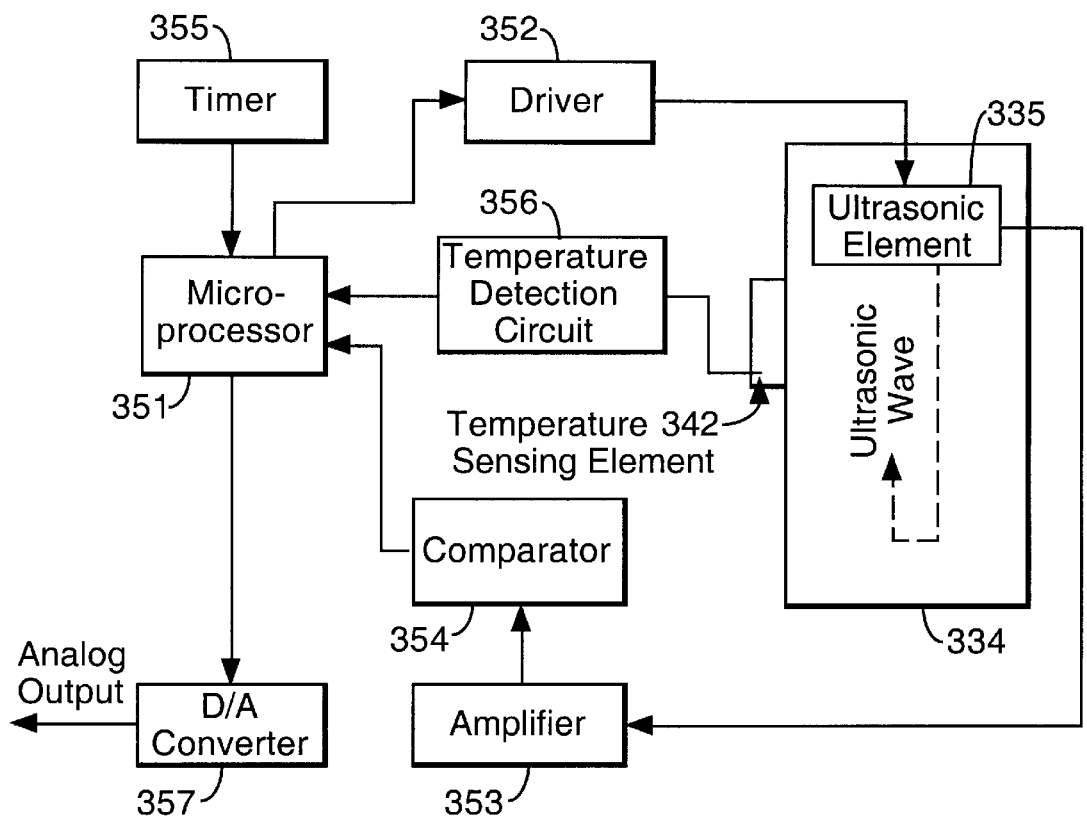
FIG. 14 is a block diagram showing the electrical configuration of a gas concentration sensor.

As shown in a block diagram of FIG. 14, a microcomputer 351 is used to drive the gas concentration sensor 325 and to perform arithmetic operations.

At the time of transmission of an ultrasonic wave, voltage is applied to the ultrasonic element 335 by use of a driver 352, to thereby transmit the ultrasonic wave. At the time of reception of an ultrasonic wave, a waveform received by the ultrasonic element 335 undergoes predetermined amplification at an amplifier 353 and is then shape-corrected at a comparator 354. The thus-shape-corrected signal is input to the microprocessor 351. The microprocessor 351 measures the propagation time between transmission and reception of the ultrasonic wave by use of a timer 355. The temperature-sensing element 342 detects the temperature of intake air within the measurement chamber 334 and transmits information regarding the detected temperature to the microprocessor 351 via a temperature detection circuit 356. On the basis of the measured propagation time and intake air temperature, the microprocessor 351 performs an arithmetic operation while referring to a map mentioned above in the section of the first embodiment, so as to convert the propagation time to hydrogen gas concentration. The thus-obtained hydrogen gas concentration is output via a D/A converter 357.

An effect of the distance L3 and the distance L3' on the measurement accuracy of the gas concentration sensor was experimented with. The distance L3 is a distance between the outer surface of the ultrasonic element 335 and a central portion of the reflection surface 336. The distance L3' is a distance between the outer surface of the ultrasonic element 335 and the bottom surface of the depression 336a formed on the reflection surface 336. The experiment was carried out while the distance L3 and the distance L3' were varied. The experiment will be described below with reference to FIGS. 15 to 20.

Figure 15:
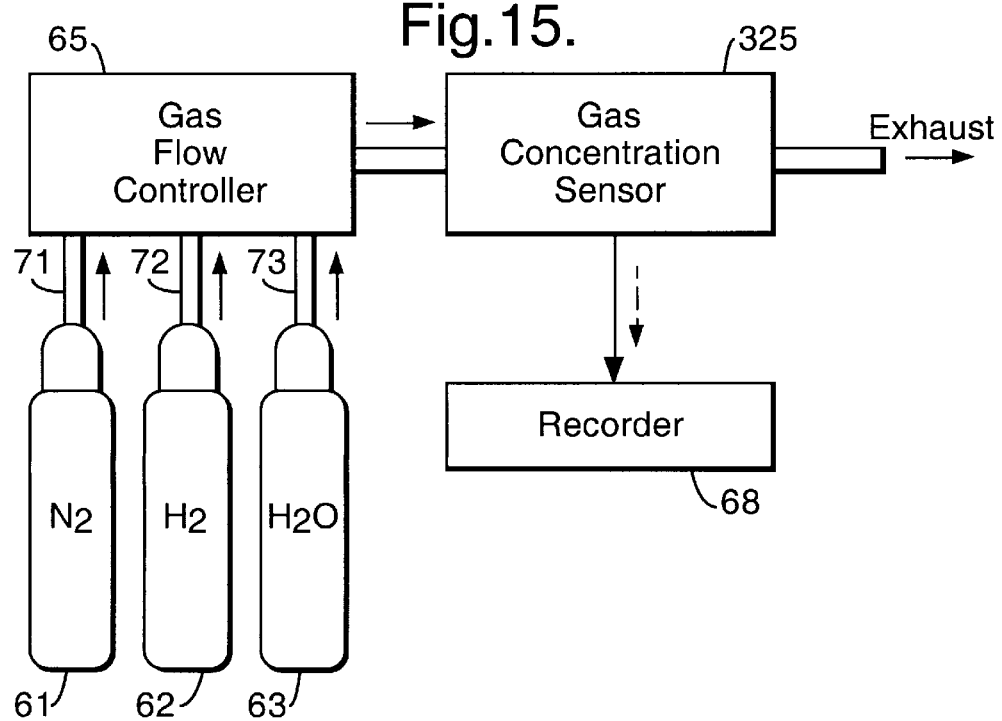
FIG. 15 is a view for explaining the configuration of experimental equipment employed in experiments.

This experiment used laboratory equipment as shown in FIG. 15. A gas under measurement having a known hydrogen gas concentration was supplied into the measurement chamber 334 of the gas concentration sensor 325 so as to measure the hydrogen gas concentration of the gas under measurement by means of the gas concentration sensor 325.

As shown in FIG. 15, nitrogen gas ($N_2$) contained in a nitrogen gas tank 61, hydrogen gas ($H_2$) contained in a hydrogen gas tank 62, and water vapor ($H_2O$) contained in a water vapor tank 63 were supplied to a gas flow controller 65 through a first line 71, a second line 72, and a third line 73, respectively. The gas flow controller 65 controls the flow rate of nitrogen gas, hydrogen gas, and water vapor so as to mix nitrogen gas, hydrogen gas, and water vapor at predetermined mixing ratios. The resultant mixed gas was supplied to the gas concentration sensor 325 through a fourth line 74 so as to introduce the mixed gas into the measurement chamber 334 of the gas concentration sensor 325 through the inflow path 337. The introduced mixed gas flowed out from the measurement chamber 334 through the outflow path 338.

In this experiment, the mixed gas flowing into the measurement chamber 334 served as a gas under measurement. The gas concentration sensor 325 measured the propagation time of an ultrasonic wave and the temperature of the mixed gas to thereby determine a hydrogen gas concentration (Xk) in the mixed gas. The results of measurement were recorded by means of a recorder 68.

Figure 16A:
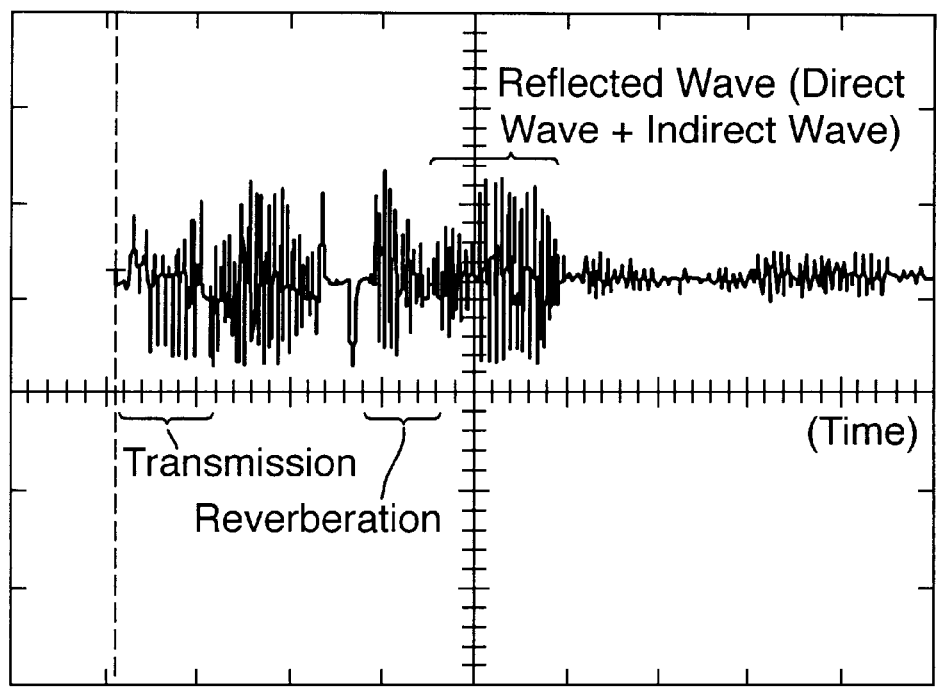
FIG. 16(a) is a view showing a transmitted/received wave in the case of a distance L3 less than 60 mm.
Figure 16B:
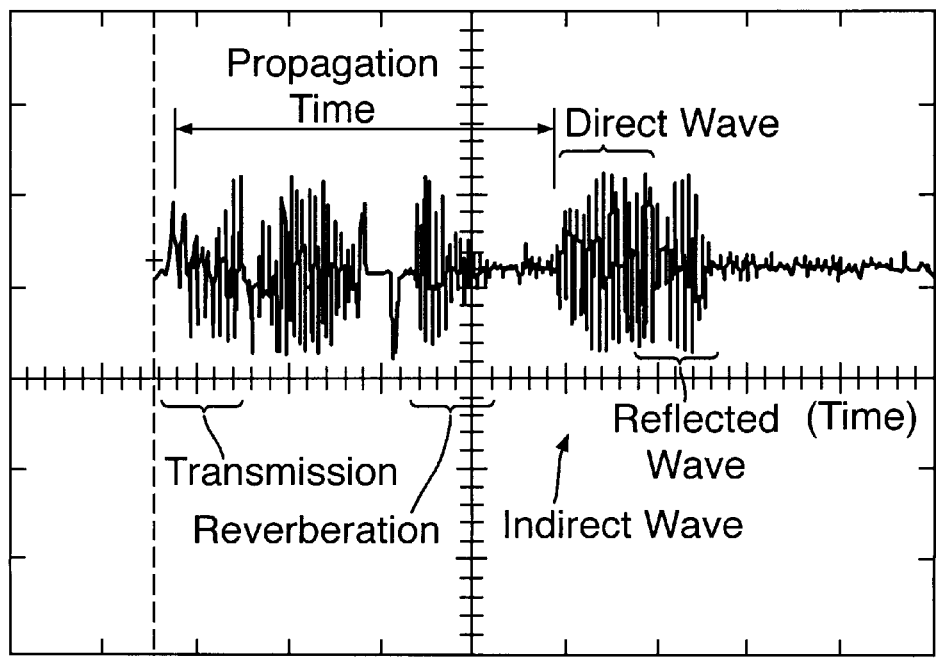
FIG. 16(b) is a view showing a transmitted/received wave in the case of a distance L3 not less than 60 mm combined with a distance L3' not less than 18 mm.

FIGS. 16(a) and 16(b) exemplify received waveforms of an ultrasonic wave. FIG. 16(a) shows a received waveform associated with a conventional gas concentration sensor having a distance L3 of 45 mm and a distance L3' of 2 mm. FIG. 16(b) shows a received waveform associated with the gas concentration sensor of the present embodiment having a distance L3 of 60 mm and a distance L3' of 18 mm. Measuring conditions are as follows: gas temperature: 100° C.; composition of mixed gas: hydrogen gas (58%), water vapor (24%), nitrogen gas (balance).

As seen from FIG. 16(a), in the case of a distance L3 of 45 mm combined with a distance L3' of 2 mm, a reverberation portion of an ultrasonic wave transmitted from the ultrasonic element 335 overlaps with a front-half portion of a reflected wave (direct wave). This indicates that, when the arrival of the reflected wave is to be detected through detection of the lead position of the reflected wave, detection of the lead position becomes difficult.

Further, in the reflected wave, a latter-half portion of the direct wave overlaps with an indirect wave. This indicates that, when the arrival of the reflected wave is to be detected through detection of a modulation point of the direct wave, detection of the modulation point becomes difficult.

Figure 21A:
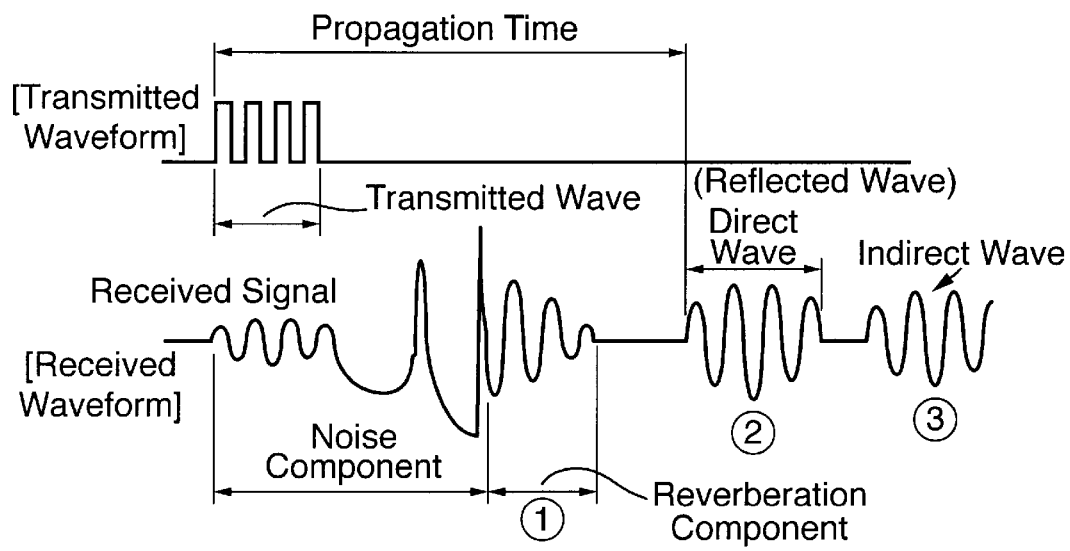
FIG. 21(a) is a view showing a transmitted/received wave in the case of a low speed of sound.
Figure 21B:
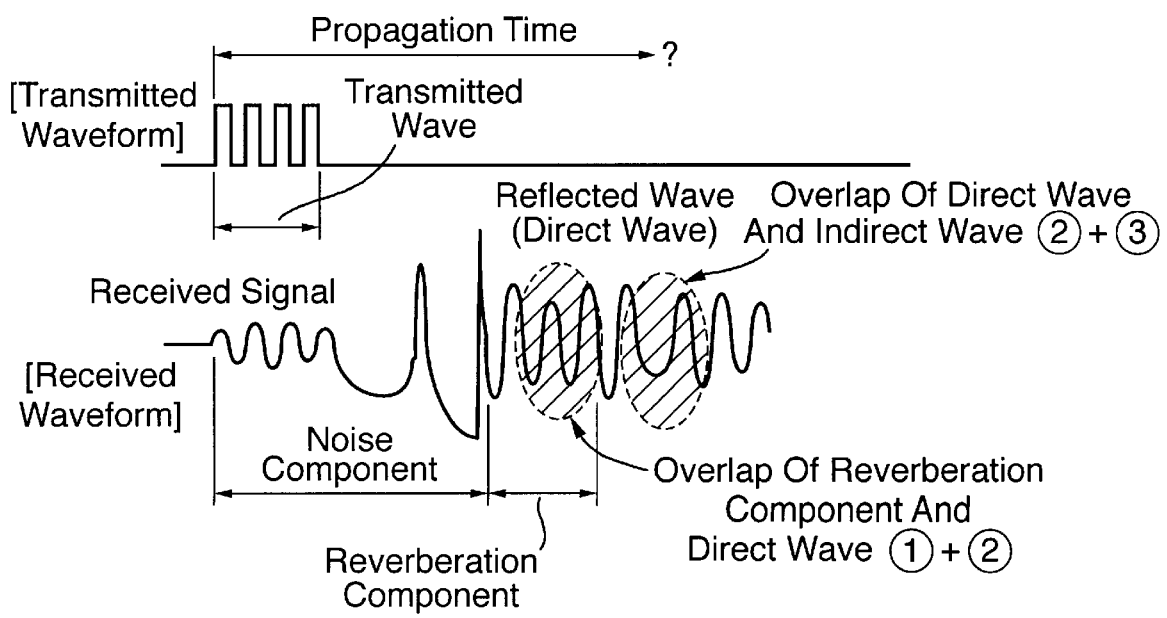
FIG. 21(b) is a view showing a transmitted/received wave in the case of a high speed of sound.
Figure 22A:
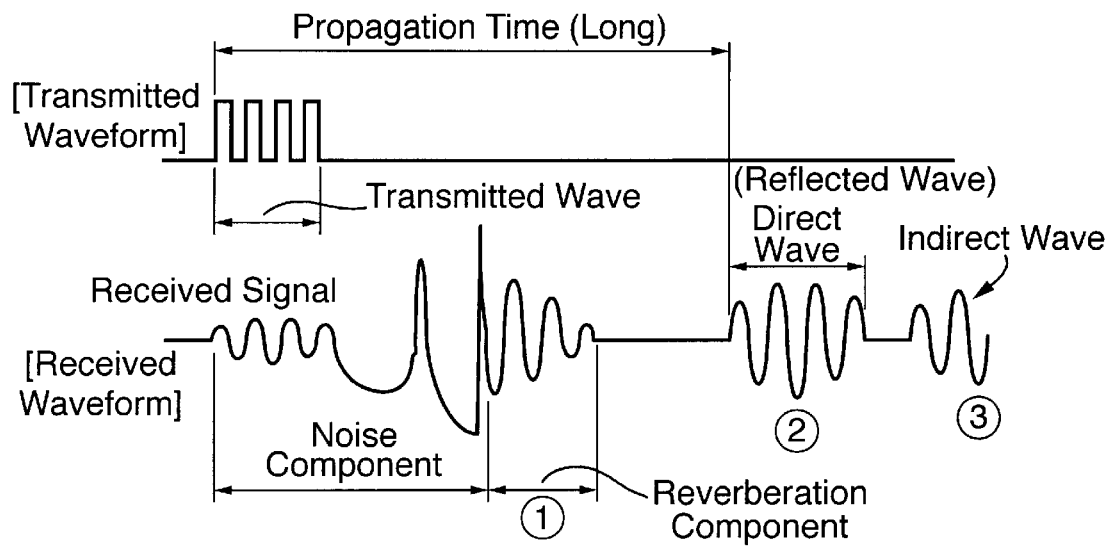
FIG. 22(a) is a view showing a transmitted/received wave in the case of a low speed of sound.
Figure 22B:
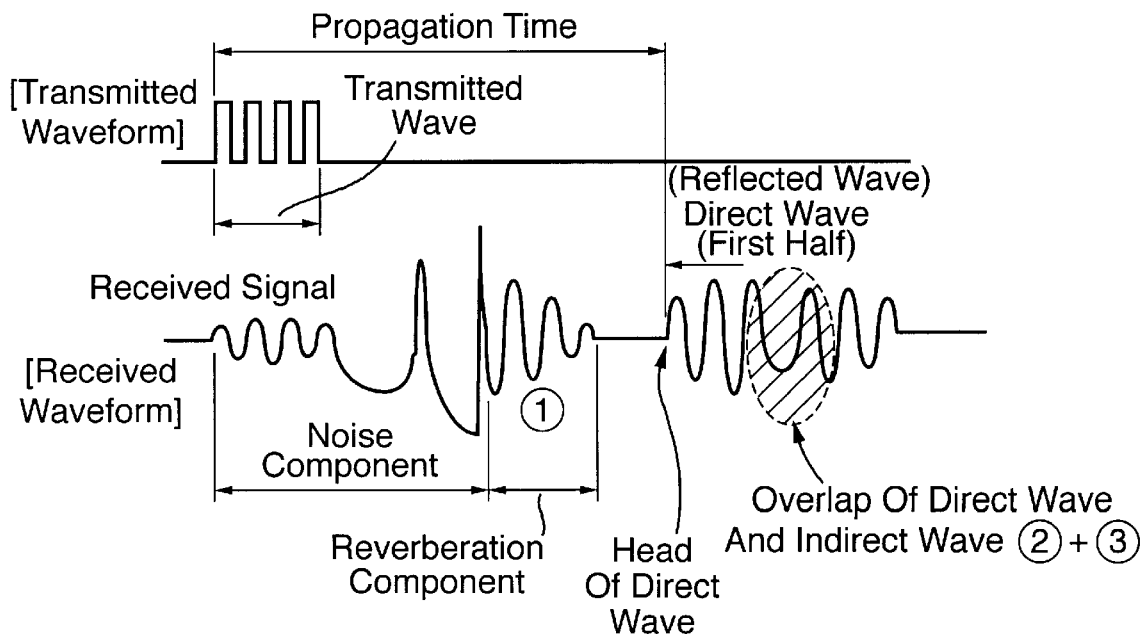
FIG. 22(b) is a view showing a transmitted/received wave in the case of a high speed of sound.

Conceivably, these problems are caused by a high speed of sound, which, in turn, caused by the fact that hydrogen gas, which has a low molecular weight, is a gas under measurement. This state corresponds to that which is schematically shown in FIG. 21(b).

A conceivable reason for overlap of a reverberation component and the reflected wave is as follows. Since an ultrasonic wave propagates at a high speed of sound, the propagation time of the ultrasonic wave (a time interval between transmission of the ultrasonic wave from the ultrasonic element 335 and reception by the ultrasonic element 335 of the ultrasonic wave reflected from the reflection surface 336) fails to become sufficiently long. As a result, before a reverberation component of the ultrasonic wave transmitted from the ultrasonic element 335 converges, the reflected wave reaches the ultrasonic element 335.

A conceivable reason for overlap of the direct wave and the indirect wave is as follows. Since an ultrasonic wave propagates at a high speed of sound, and the distance L3' (depth of the depression 336a) is not sufficiently long, a time interval between the direct wave and the indirect wave fails to become sufficiently long. As a result, before arrival of the direct wave at the ultrasonic element 335 is completed, the indirect wave reaches the ultrasonic element 335.

Figure 17:
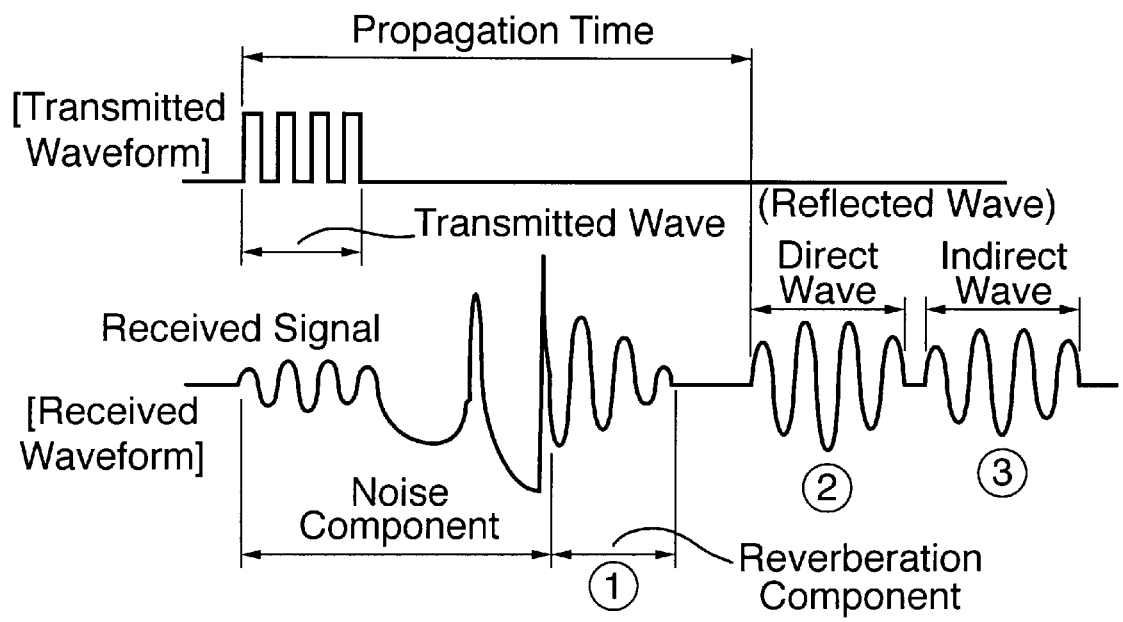
FIG. 17 is a schematic view showing a transmitted/received waveform in the case of a distance L3 not less than 60 mm combined with a distance L3' not less than 18 mm.

By contrast, the above-mentioned problems do not arise in the case of a distance L3 of 60 mm combined with a distance L3' of 18 mm. This state is schematically shown in FIG. 17. There is a constant time interval between detection of a reverberation component and detection of a reflected wave (direct wave) and between detection of the direct wave (a component of the reflected wave) and detection of an indirect wave (a component of the reflected wave).

The reason why the reverberation component and the reflect wave do not overlap each other is as follows. Because of employment of a distance L3 of 60 mm, the propagation distance of the reflected wave is lengthened, so that the reflected wave arrives after the reverberation component is converged. As a result, the reverberation component does not overlap with the reflected wave. Particularly, when the arrival of the reflected wave is to be detected through detection of the lead position of the reflected wave, the arrival of the reflected wave can be detected accurately.

The reason why the reflect wave and the indirect wave o not overlap each other is as follows. Because of employment of a distance L3' of 18 mm, the difference in propagation distance between the direct wave and the indirect wave increases, so that the indirect wave arrives after the arrival of the direct wave. As a result, the indirect wave does not overlap with the direct wave. Particularly, when the arrival of the reflected wave is to be detected through detection of a modulation point of the direct wave, the arrival of the reflected wave can be detected accurately.

Figure 18:
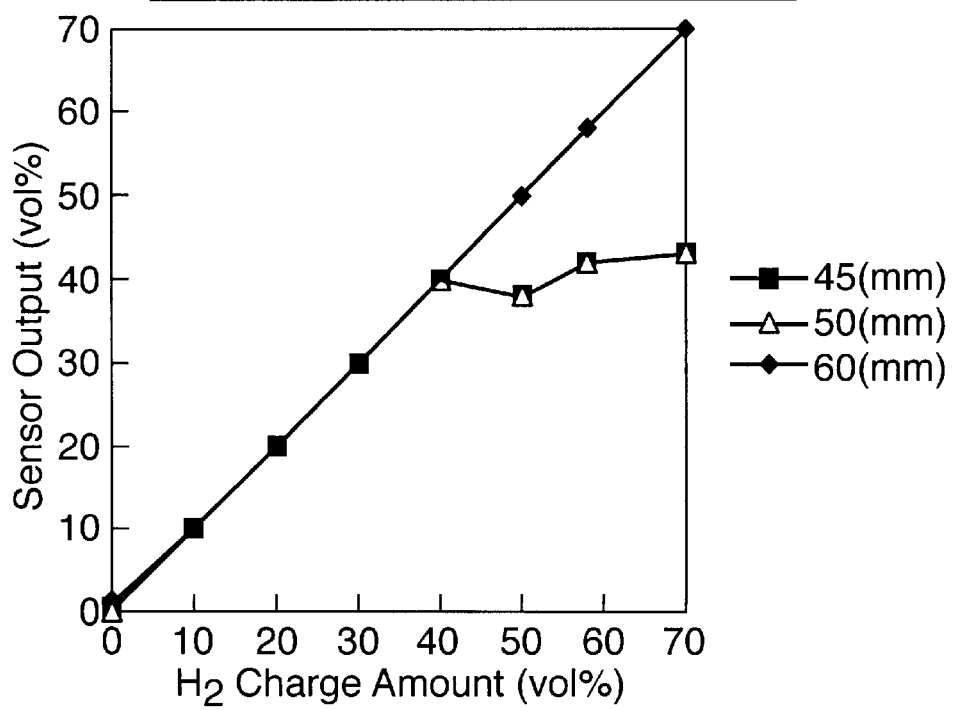
FIG. 18 is a graph showing the relationship between a charge amount of hydrogen (set concentration) and a sensor output (measured concentration) as obtained through experiment conducted while the distance L3 is varied.
Figure 19:
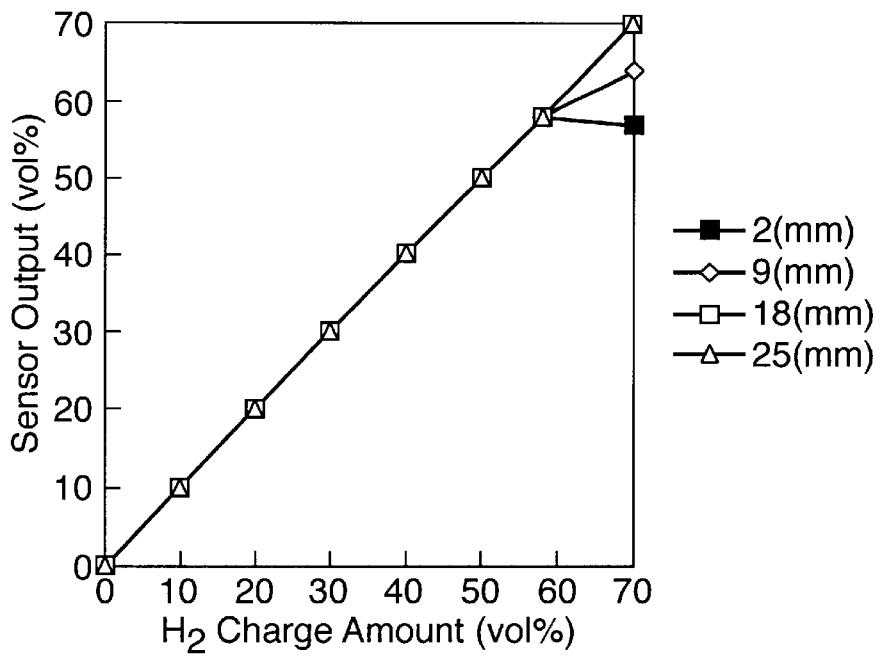
FIG. 19 is a graph showing the relationship between a charge amount of hydrogen (set concentration) and a sensor output (measured concentration) as obtained through experiment conducted while the distance L3' is varied.
Figure 20:
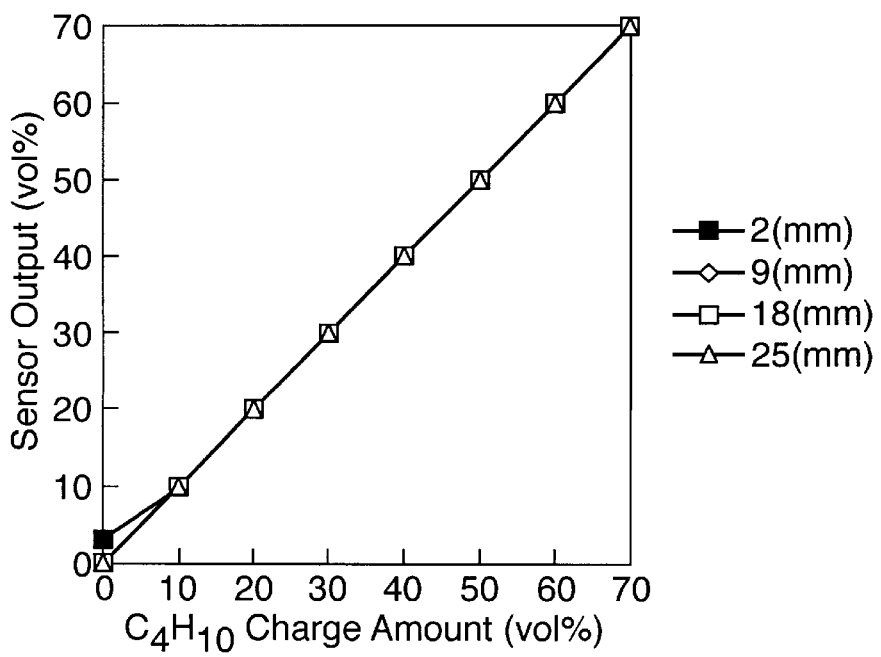
FIG. 20 is a graph showing the relationship between a charge amount of butane (set concentration) and a sensor output (measured concentration) as obtained through experiment conducted while the distance L3' is varied.

FIGS. 18 to 20 show the results of measuring an output from the gas concentration sensor while the distance L3 and the distance L3' are varied.

FIG. 18 shows the relationship between a charge amount of hydrogen (set concentration) and a sensor output (measured concentration) at a distance L3 of 45 mm, 50 mm, and 60 mm.

A mixed gas used in this experiment has the following composition: water vapor (24%), hydrogen gas (0% to 70% variable), and nitrogen gas (balance). The distance L3' was set to 2 mm. Propagation time was determined as a time interval between the lead position of a transmitted wave and the lead position of a received wave (reflected wave).

As shown in FIG. 18, when the distance L3 is 60 mm, the gas concentration sensor 325 outputs an accurate value in relation to a charge amount of hydrogen gas ($H_2$). That is, even when the speed of sound increases with hydrogen gas concentration, the gas concentration sensor 325 outputs hydrogen gas concentration accurately. By contrast, when the distance L3 is 45 mm or 50 mm, the accuracy of the gas concentration sensor 325 is impaired at a charge amount of hydrogen gas in excess of 40%, indicating that hydrogen gas concentration cannot be determined accurately.

Since the speed of sound increases with the concentration of hydrogen gas concentration, which has a low molecular weight, the propagation time of an ultrasonic wave fails to become sufficiently long at a distance L3 of 45 mm or 50 mm. As a result, reverberations and a controller's switching noise which are generated at the time of transmission of an ultrasonic wave overlap with a reflected wave propagating from the reflection surface, thereby preventing accurate reception of the reflected wave.

By contrast, when the distance L3 is 60 mm, the propagation time of an ultrasonic wave can become sufficiently long, thereby preventing the above problem.

Notably, in the present experiment, even when the distance L3' is as small as 2 mm (less than 18 mm), an accurate sensor output is obtained even at high hydrogen gas concentration. This is because propagation time is not measured on the basis of a modulation point but is measured on the basis of the lead position of a waveform component. Thus, even when a latter-half portion of the direct wave overlaps with the indirect wave, no problem arises with respect to measurement of propagation time.

FIG. 19 shows the results of measuring the relationship between a charge amount of hydrogen gas and a sensor output at a distance L3' of 2 mm, 9 mm, 18 mm, and 25 mm while the distance L3 is fixed to 60 mm.

As in the above-described experiment, a mixed gas used in this experiment has the following composition: water vapor (24%), hydrogen gas (0% to 70% variable), and nitrogen gas (balance). Propagation time was determined as a time interval between a modulation point of a transmitted wave and a modulation point of a received wave (reflected wave).

As seen from FIG. 19, when the distance L3' is 18 mm or 25 mm, the gas concentration sensor 325 outputs an accurate value in relation to a charge amount of hydrogen gas.

By contrast, when the distance L3' is 2 mm or 9 mm, the accuracy of the gas concentration sensor 325 is impaired at a charge amount of hydrogen gas in excess of about 60%, indicating that hydrogen gas concentration cannot be determined accurately.

Since the speed of sound increases with hydrogen gas concentration, there cannot be a sufficient difference in propagation time between the direct wave and the indirect wave at a distance L3' of 2 mm or 9 mm. As a result, the indirect wave overlaps with the direct wave in the position of a modulation point of the direct wave, thereby preventing accurate reception of the reflected wave. By contrast, when the distance L' is 18 mm or 25 mm, there can be a sufficient difference in propagation time between the direct wave and the indirect wave, thereby preventing such a problem.

As described above, according to the present embodiment, the measurement chamber 334 provides a sufficiently long propagation distance or a sufficiently long propagation path so as to elongate the propagation time of an ultrasonic wave, whereby reception is not susceptible to transmission to thereby accurately determine the propagation time of an ultrasonic wave. As a result, the gas concentration sensor of the present embodiment can be applied effectively to measurement of the concentration of a gas having a low molecular weight, such as hydrogen gas.

FIG. 20, for comparison with FIG. 19, shows the results of measuring the relationship between a charge amount of butane ($C_4H_{10}$) and a sensor output at a distance L3' of 2 mm, 9 mm, 18 mm, and 25 mm while the distance L3 is fixed to 60 mm. Experimental conditions are similar to those described above except that butane replaces hydrogen gas.

Since butane has a molecular weight higher than that of hydrogen gas, the speed of sound does not increase considerably with butane concentration. Thus, as shown in FIG. 20, even when the distance L3' assumes a minimum value of 2 mm, the indirect wave does not overlap with the direct wave even at high butane concentration, and butane concentration is detected accurately.

However, at a charge amount of butane not greater than 10%, measured values as obtained at a distance L3' of 2 mm show some error. Contrary to the above-described case of hydrogen gas, an ultrasonic wave propagates at a low speed due to a low speed of sound. As a result, before reflection of a latter-half portion of the direct wave from the reflection surface is completed, the indirect wave reflects from the reflection surface to thereby overlap with the direct wave.

Thus, preferably, even when the speed of sound is relatively low, the distance L3' is set to a certain large value.

Fourth Embodiment

A fourth embodiment of the invention will now be described.

Items corresponding to those of the embodiment shown in FIG. 13 are given like reference numerals.

Figure 23:
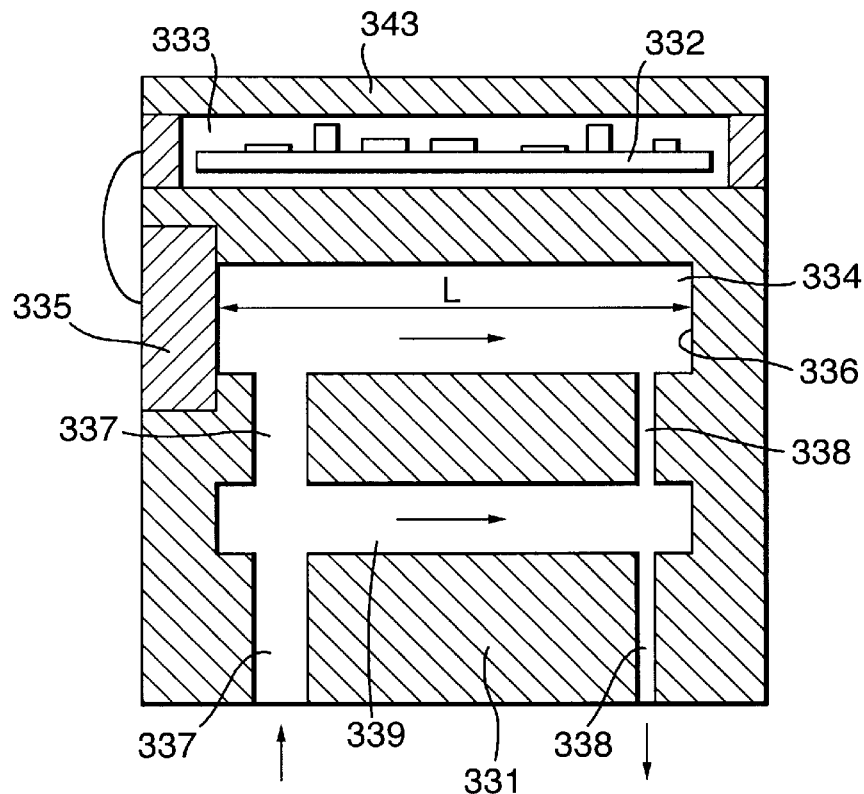
FIG. 23 is a schematic sectional view showing the entire structure of a gas concentration sensor according to a fourth embodiment of the invention.

The gas concentration sensor 325 assumes a structure shown in FIG. 23. Specifically, a sensor casing 331 is a body of the gas concentration sensor 325 and assumes an integral structure formed of metal or resin. The sensor casing 331 includes a circuit-board enclosing chamber 333 in which a drive-arithmetic circuit 332 is disposed; a measurement chamber 334 into which intake air which includes vaporized fuel is introduced; an ultrasonic transmitter-receiver element (hereinafter referred to merely as an ultrasonic element) 335 disposed on one of two end wall surfaces which face each other within the measurement chamber 334; a reflection surface 336 implemented by the other end wall surface which faces the end wall surface on which the ultrasonic element 335 is disposed, located a predetermined distance L away from the ultrasonic element 335, and adapted to reflect an ultrasonic wave transmitted from the ultrasonic element 335; an inflow path 337 adapted to allow the intake air to flow into the measurement chamber 334 from outside the sensor casing 331; an outflow path 338 adapted to allow the intake air to flow out from the measurement chamber 334 to the exterior of the sensor casing 331; and a bypass path 339 disposed in parallel with the measurement chamber 334 and adapted to connect a portion of the inflow path 337 located upstream of a portion of connection with the measurement chamber 334, and a portion of the outflow path 338 located downstream of a portion of connection with the measurement chamber 334. After the drive-arithmetic circuit 332 is installed within the circuit-board enclosing chamber 333, the chamber 333 is sealed by means of a circuit cover 343. The diameter of the outflow path 338 is smaller than that of the inflow path 337. Specifically, the diameter of the outflow path 338 is 2 mm, whereas the diameter of the inflow path 337 is 4.8 mm.

In the gas concentration sensor 325 of the present embodiment, the diameter of the outflow path 338 is smaller than that of the inflow path 337, and the bypass path 339 extends between the inflow path 337 and the outflow path 338. Thus, even when intake air, or purge gas, flows at high velocity through piping in which the gas concentration sensor 325 is installed, a modulation point can be detected accurately.

Figure 24:
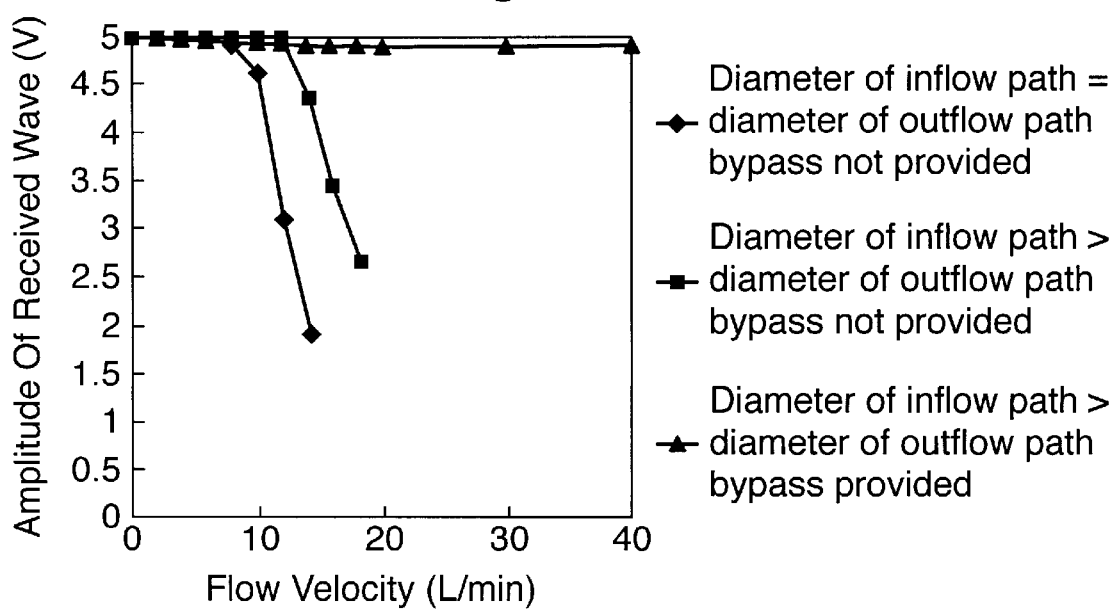
FIG. 24 is a graph showing the experimentally obtained relationship between the amplitude of a received wave and the velocity of intake air flowing through piping in which the gas concentration sensor is installed.

FIG. 24 shows the results of an experiment performed to examine the relationship between the maximum amplitude of a received wave and the flow velocity of intake air as measured at an end portion of the inflow path 337, under the following conditions: (1) the diameter of the inflow path 337 is equal to that of the outflow path 338, and the bypass path 339 is not provided; (2) the diameter of the outflow path 338 is smaller than that of the inflow path 337, and the bypass path 339 is not provided; and (3) the diameter of the outflow path 339 is smaller than that of the inflow path 337, and the bypass path 339 is provided (i.e., in the case of the present embodiment).

Figure 25:
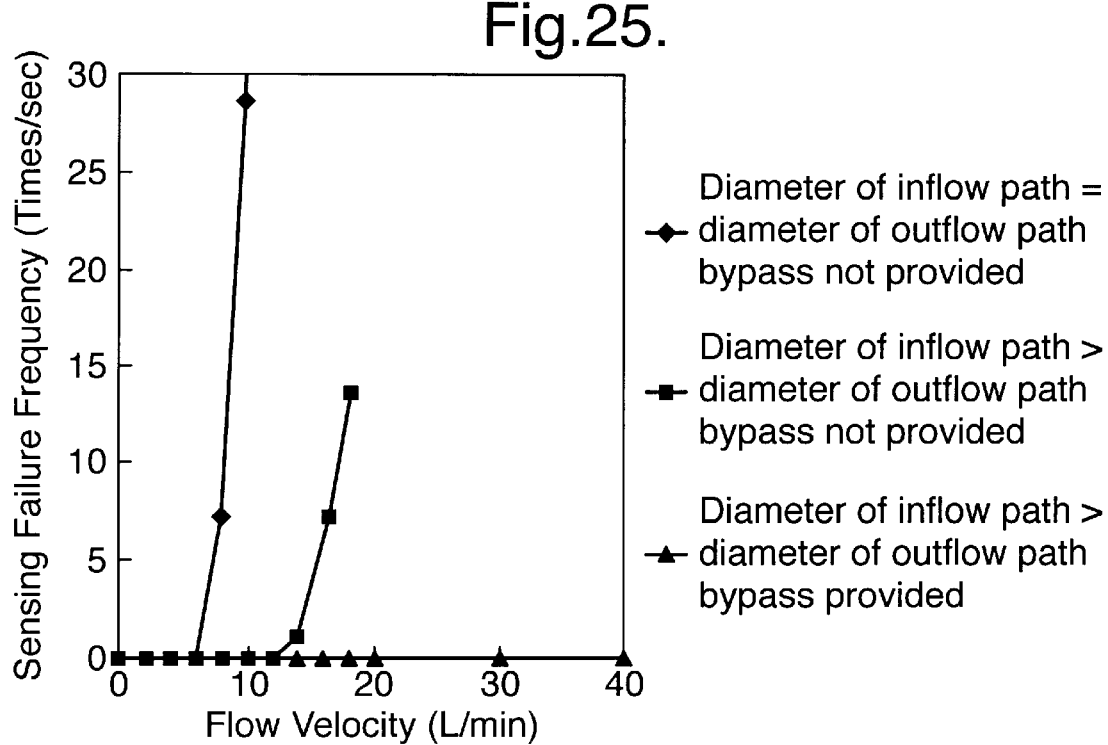
FIG. 25 is a graph showing the experimentally obtained relationship between sensing failure frequency and the velocity of intake air flowing through piping in which the gas concentration sensor is installed.

FIG. 25 shows the results of an experiment performed to examine the relationship between a sensing failure frequency (times/sec) with respect to a modulation point as observed in the drive-arithmetic circuit 332 and the flow velocity of intake air as measured at an end portion of the inflow path 337, under the above conditions (1) to (3).

In the case of the condition (1) corresponding to the conventional gas concentration sensor 325, the inflow path 337 and the outflow path 338 have a diameter of 4.8 mm. In the case of the conditions (2) and (3), the outflow path 338 has a diameter of 2 mm, while the inflow path 337 has a diameter of 4.8 mm.

Herein, an end portion of the inflow path 337 means that located in opposition to the measurement chamber 334. The flow velocity of intake air as measured at an end portion of the inflow path 337 means the velocity of intake air, or vaporized fuel, flowing through piping in which the gas concentration sensor 325 is installed. Specifically, in the case of the first through third gas concentration sensors 21 to 23 shown in FIG. 1, the flow velocity of intake air as measured at an end portion of the inflow path 337 means the flow velocity of vaporized fuel flowing respectively through the second supply path 13, the canister 14, and the third supply path 16 extending between the canister 14 and the purge valve 17. In the case of the fourth gas concentration sensor 24, the flow velocity of intake air as measured at an end portion of the inflow path 337 means the flow velocity of intake air which contains purge gas and flows through the intake pipe 2. Intake air attempts to enter the inflow path 337 through an end portion of the inflow path 337 (located in opposition to the measurement chamber 334) at a flow velocity proportional to that as measured in piping in which the gas concentration sensor 325 is installed.

At this time, the flow velocity of intake air within the measurement chamber 334 varies depending on a gas flow and a gas flow resistance in the inflow path 337 connected to the measurement chamber 334 and those in the outflow path 338 connected to the measurement chamber 334 as well as depending on a gas flow which branches off to the bypass path 339.

As shown in FIG. 24, in the case of the conventional gas concentration sensor 325 corresponding to the condition (1) in which the inflow path 337 and the outflow path 338 have the same diameter, the maximum amplitude of a received wave attenuates abruptly when the flow velocity of intake air as measured at an end portion of the inflow path 337 exceeds 6 liters/min. This is because, as the velocity of intake air flowing through piping in which the gas concentration sensor 325 is installed increases, the flow velocity of intake air within the measurement chamber 334 increases abruptly. In this case, an intake air flow within the measurement chamber 334 is disturbed. As a result, an ultrasonic wave propagating in the intake air within the measurement chamber 334 suffers unstable amplitude attenuation.

FIG. 25 shows that, due to abrupt attenuation of the amplitude of a received wave, the conventional gas concentration sensor 325 corresponding to the condition (1) suffers a frequent failure to measure propagation time. Since the ultrasonic element 335 fails to receive a reflected wave which has a sufficient intensity to identify a modulation point, the propagation time of an ultrasonic wave propagating within the measurement chamber 334 cannot be measured accurately.

By contrast to the conventional gas concentration sensor 325 corresponding to the condition (1), in the case of the condition (2) in which the diameter of the outflow path 338 is smaller than that of the inflow path 337, as shown in FIGS. 24 and 25, the maximum amplitude of a received wave does not attenuate, and thus a sensing failure with respect to a modulation point does not occur until the flow velocity of intake air as measured at an end portion of the inflow path 337 becomes 12 liters/min. This is because the diameter of the outflow path 338 is smaller than that of the inflow path 337, causing an increase in a gas flow resistance in the outflow path 338. As compared to the gas concentration sensor 325 corresponding to the condition (1), the gas concentration sensor 325 corresponding to the condition (2) can delay the occurrence of an intake air flow disturbance within the measurement chamber 334 until the flow velocity reaches a higher value. That is, as compared to the gas concentration sensor 325 corresponding to the condition (1), the gas concentration sensor 325 corresponding to the condition (2) can suppress an increase in the flow velocity of intake air within the measurement chamber 334 to a greater extent. Accordingly, the gas concentration sensor 325 corresponding to the condition (2) can detect a modulation point more accurately and thus can measure the propagation time of an ultrasonic wave more accurately, enabling highly accurate determination of gas concentration.

In the case of the condition (3) in which the bypass path 339 is provided in the gas concentration sensor 325 corresponding to the condition (2), as shown in FIGS. 24 and 25, the maximum amplitude of a received wave does not attenuate, and thus a sensing failure with respect to a modulation point does not occur until the flow velocity of intake air as measured at an end portion of the inflow path 337 becomes 40 liters/min. This is because, in the gas concentration sensor 325 corresponding to the condition (3), the diameter of the outflow path 338 is smaller than that of the inflow path 337, causing an increase in a gas flow resistance in the outflow path 338 and causing a gas flow directed to the measurement chamber 334 to sufficiently branch to the bypass path 339. As compared to the gas concentration sensor 325 corresponding to the condition (2), the gas concentration sensor 325 corresponding to the condition (3) can delay the occurrence of an intake air flow disturbance within the measurement chamber 334 until the flow velocity reaches a higher value. That is, as compared to the gas concentration sensor 325 corresponding to the condition (2) in which the diameter of the outflow path 338 is made smaller than that of the inflow path 337 without formation of the bypass path 339, the gas concentration sensor 325 corresponding to the condition (3) (i.e., the gas concentration sensor 325 of the present embodiment) can suppress an increase in the flow velocity of intake air within the measurement chamber 334 to a greater extent. Accordingly, the gas concentration sensor 325 corresponding to the condition (3) can detect a modulation point more accurately and thus can measure the propagation time of an ultrasonic wave more accurately, enabling highly accurate determination of gas concentration.

Fifth Embodiment

A fifth embodiment of the invention will now be described. Items corresponding to those of preceding embodiments are given like reference numerals.

Figure 26:
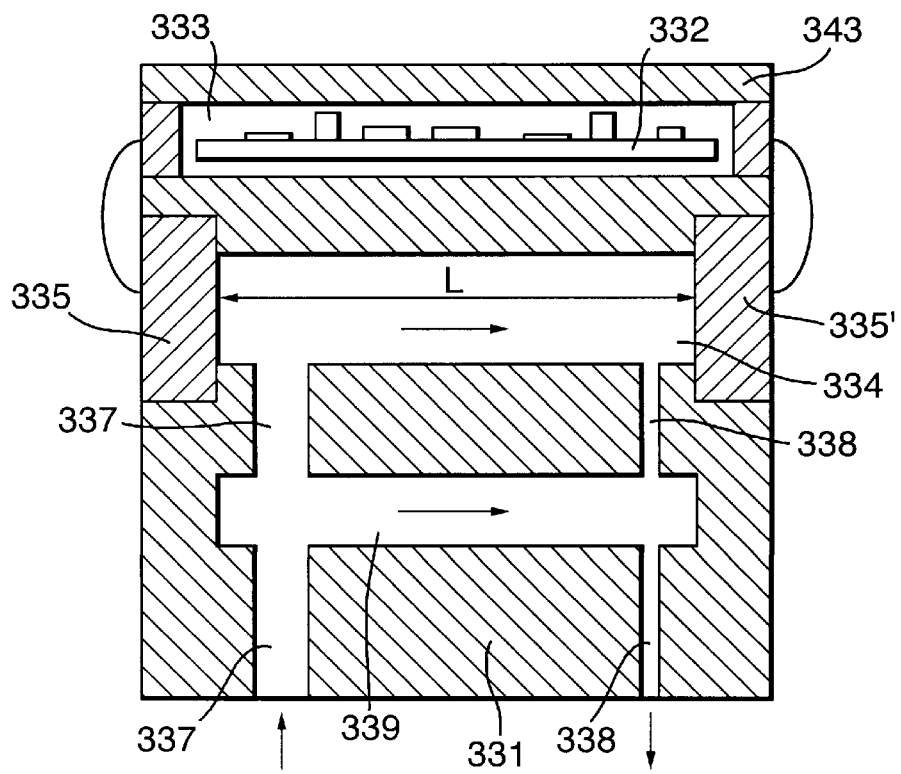
FIG. 26 is a schematic sectional view showing the entire structure of a gas concentration sensor according to a fifth embodiment of the invention.

The above fourth embodiment is described while mentioning the ultrasonic element 335 disposed on only one of two end wall surfaces which face each other within the measurement chamber 334. However, as shown in FIG. 26, ultrasonic elements 335 and 335' may be disposed respectively on two end wall surfaces which face each other within the measurement chamber 334. In this case, one ultrasonic element 335 is adapted to transmit an ultrasonic wave, while the other ultrasonic element 335' is adapted to receive the ultrasonic wave. Both of the ultrasonic elements 335 and 335' assume a structure shown in FIG. 2(b).

The gas concentration sensor 325 in this case is different from the gas concentration sensor 325 of the fourth embodiment in the following points.

First, in the gas concentration sensor 325 in this case, the drive-arithmetic circuit 332 shown in FIG. 3 does not include the transmission-reception changeover switches 52a and 52b. The driver is only connected to the ultrasonic element 335 for transmission use. Only the ultrasonic element 335' for reception use is connected to the amplifier 53.

When an L represents the distance between the outer surfaces of the two ultrasonic elements 335 and 335', the drive-arithmetic circuit 332 in this case calculates the speed of sound C in the following manner.

First, when the ultrasonic element 335 for transmission use transmits through the driver, for example, an ultrasonic wave involving frequency modulation as shown in FIG. 6, a frequency change similar to that in a transmitted wave is reflected in an ultrasonic wave received by the ultrasonic element 335' for reception use. When the speed of sound C is to be obtained from a propagation time t1 between a modulation point of the transmitted wave from the ultrasonic element 335 and a modulation point of a first received wave arriving at the ultrasonic element 335', a propagation distance becomes L, which is different from the case of the above-described embodiment. The speed of sound C is calculated by use of the following expression (3).

$$C = L(\text{distance between two element surfaces})/t1(\text{propagation time}) \quad (3)$$

Even in this case where the ultrasonic elements 335 and 335' are employed, the first propagation time t1 involves a lag caused by, for example, time-course deterioration of the molded material 42. In this case, a first arrival time t1 (first propagation time t1) between a modulation point of the transmitted wave and a modulation point of the first received wave, which arrives first time at the ultrasonic element 335' for reception use, is measured. Also, a second arrival time t3 between the modulation point of the transmitted wave and a modulation point of an ultrasonic wave which arrives second time at the ultrasonic element 335' (i.e. an ultrasonic wave which is reflected from the surface of the ultrasonic element 335' upon first arrival at the ultrasonic element 335' and is then reflected from the surface of the ultrasonic element 335, and is then again detected by the ultrasonic element 335') is measured. The first arrival time t1 is subtracted from the second arrival time t3 to thereby obtain a time t2 (second propagation time t2) which is required for the ultrasonic wave to propagate back and forth between the ultrasonic elements 335 and 335' after being reflected first time from the surface of the ultrasonic element 335'. Since the ultrasonic wave which has arrived first time at the ultrasonic element 335' propagates back and forth simply in a similar manner between the two ultrasonic elements 335 and 335' to reach again the ultrasonic element 335', the second propagation time t2 is free from influence of time-course deterioration. Notably, the drive-arithmetic circuit 332 calculates the speed of sound C by use of the following expression (4).

$$C = 2L(\text{distance to propagate back and forth between two element surfaces})/t2(\text{propagation time}) \quad (4)$$

That is, the gas concentration sensor 325 uses the expression (3) only when the speed of sound C is to be obtained from the first propagation time t1. When the speed of sound C is to be obtained from the (n+1)th propagation time $t_{n+1}$ (n is an integer of 1 or greater), the expression (4) is used (in this case, "t2 (propagation time)" in the expression (4) is read as "$t_{n+1}$ (propagation time)").

When the (n+1)th propagation time $t_{n+1}$ is to be obtained, the nth arrival time $t_{n+1}$ is subtracted from the (n+1)th arrival time $t_{n+2}$. However, as a propagation distance increases, a reflected wave which arrives at the ultrasonic element 335' attenuates gradually. As a result, measurement accuracy impairs with n.

Alternatively, a time interval between detection of a certain modulation point by the ultrasonic element 335' and detection of the next modulation point by the ultrasonic element 335' (for example, a time interval between a modulation point of an ultrasonic wave which arrives first time at the ultrasonic element 335' and a modulation point of the ultrasonic wave which arrives second time at the ultrasonic element 335' as described above) may be directly measured. Even in this case, a similar effect is also obtained.

While the present invention has been described with reference to embodiments, the present invention is not limited thereto, but may be embodied in many other specific forms.

Figure 12A:
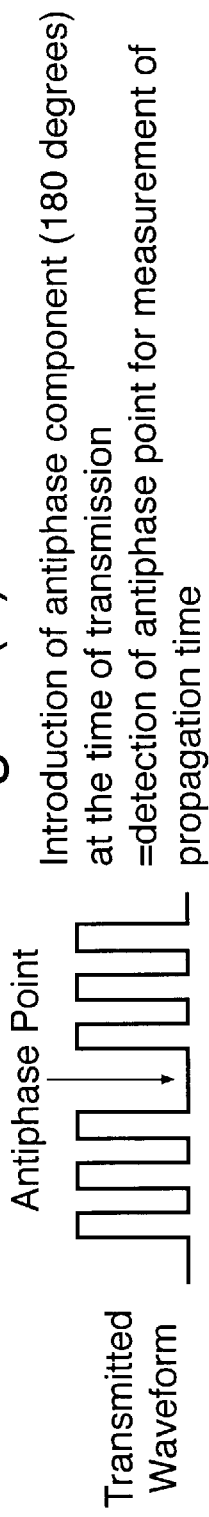
FIG. 12(a) is a view showing the transmitted waveform into which one antiphase component is introduced.

For example, the above embodiments are described while mentioning transmission of an ultrasonic wave involving frequency modulation. However, an ultrasonic wave including an antiphase component may be transmitted. For example, as shown in FIG. 12(a), when an ultrasonic wave into which an antiphase component (180 degrees) is introduced is transmitted, no signal waveform appears at an antiphase point of the transmitted wave.

Figure 12B:
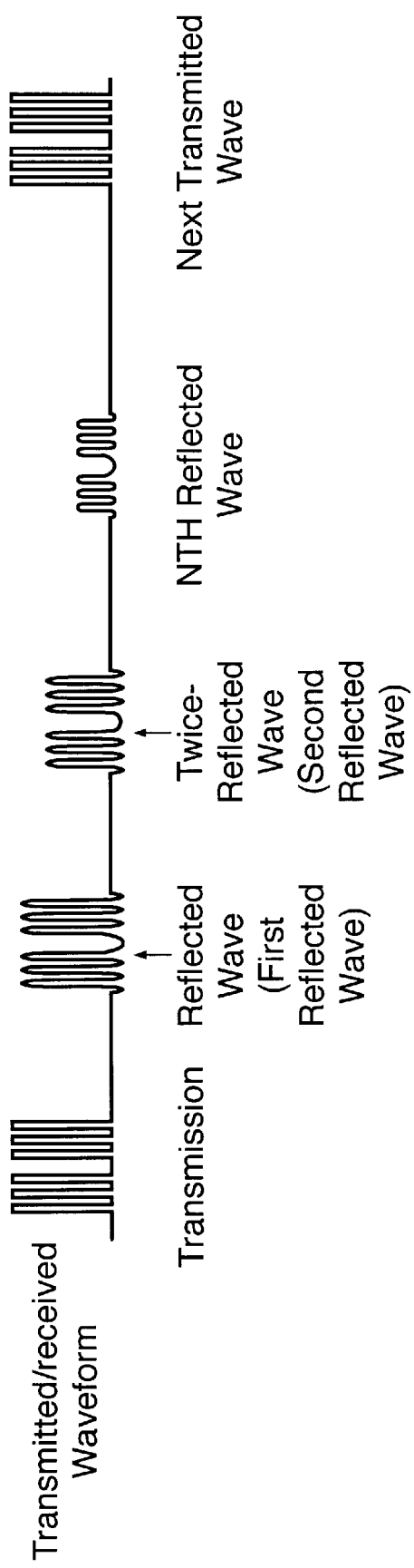
FIG. 12(b) is a timing chart showing a transmitted/received waveform.

As shown in FIG. 12(b), a received wave; i.e., a reflected wave includes a point which corresponds to the antiphase point and at which no signal waveform appears.

Accordingly, a point (modulation point) where an antiphase component is introduced may be used as a reference for measurement of propagation time as in the case of a frequency modulation point employed in the above-described embodiments, thereby determining gas concentration.

Specifically, for example, a time which has elapsed until an antiphase point of a first reflected wave appears is subtracted from a time which has elapsed until an antiphase point of a second reflected wave appears, to thereby accurately obtain the propagation time of the second reflected wave (second propagation time). On the basis of this second propagation time, gas concentration may be determined.

The third embodiment is intended to detect hydrogen gas concentration and employs a distance L3 not less than 60 mm and a distance L3' not less than 18 mm for the gas concentration sensor of FIG. 13. However, these dimensional limitations on distance are applicable to not only the gas concentration sensor of FIG. 13 but also any other gas concentration sensors for detecting hydrogen gas concentration. For example, the gas concentration sensors according to the first and second embodiments as shown in FIGS. 6 and 7 may have a distance L not less than 60 mm and a distance L' not less than 18 mm.

The third embodiment is described while mentioning hydrogen gas as a gas under measurement. However, the gas concentration sensor of the third embodiment may be used effectively with a gas having a low molecular weight other than hydrogen gas. Further, the gas concentration sensor of the third embodiment may be used with a gas having a relatively high molecular weight as compared to hydrogen gas, through experimental optimization of L3, L3', L, and L'.

Application of the above-embodied gas concentration sensors is not limited to an internal combustion engine. For example, the gas concentration sensors may be effectively applicable to measurement of the hydrogen gas concentration of a reformed gas of a fuel cell.

The features of the embodiments of the invention described herein may be used separately or in any appropriate combination.

What is claimed is:

1. A gas concentration sensor comprising:
    a measurement chamber having an inflow path for allowing inflow of gas under measurement thereinto and an outflow path for allowing outflow of the gas therefrom;
    an ultrasonic element disposed on one of two wall surfaces located in opposition to each other within said measurement chamber, and capable of transmitting an ultrasonic wave toward the other of the two wall surfaces and receiving an ultrasonic wave reflected from the wall surface serving as a reflection surface; and
    gas concentration detection means for causing said ultrasonic element to transmit an ultrasonic wave and to receive the reflected wave, for measuring a propagation time between transmission of the ultrasonic wave and reception of the reflected wave, and for determining a concentration of a specific gas contained in the gas under measurement on the basis of the propagation time,
    said sensor being characterized in that said measurement chamber is formed such that a distance between an edge portion of the reflection surface and said ultrasonic element is greater than a distance between a central portion of the reflection surface and said ultrasonic element.

2. A gas concentration sensor according to claim 1, wherein a cross-sectional area of the outflow path is smaller than a cross-sectional area of the inflow path.

3. A gas concentration sensor according to claim 1, characterized in that said measurement chamber is formed such that an edge portion of the reflection surface is formed into a depression having a bottom surface parallel to the reflection surface and such that a distance between the bottom surface of the depression and said ultrasonic element is at least 18 mm greater than a distance between a central portion of the reflection surface and said ultrasonic element.

4. A gas concentration sensor according to claim 1, wherein said gas detection means causes said ultrasonic element to transmit an ultrasonic wave so that the ultrasonic wave is reflected from the reflection surface to thereby become a first reflected wave; said gas detection means causes said ultrasonic element to reflect the first reflected wave so that the first reflected wave is again reflected from the reflection surface; and said gas detection means measures a propagation time associated with a reflected wave other than the first reflected wave so as to determine the concentration of a specific gas on the basis of the propagation time.

5. A gas concentration sensor according to claim 1, wherein a bypass path for connecting the inflow path and the outflow path is provided separately from said measurement chamber.

6. A gas concentration sensor according to claim 1, wherein said gas concentration detection means measures a propagation time between reception of an ultrasonic wave by said ultrasonic element and next reception of an ultrasonic wave by said ultrasonic element and determines the concentration of a specific gas on the basis of the propagation time.

7. A gas concentration sensor according to claim 1, wherein said gas detection means causes said ultrasonic element to transmit/receive an ultrasonic wave involving at least one frequency modulation and is adapted to determine the concentration of a specific gas on the basis of the propagation time obtained through utilization of the modulation point present in the ultrasonic wave.

8. A gas concentration sensor according to claim 1, wherein said gas detection means causes said ultrasonic element to transmit/receive an ultrasonic wave involving at least one antiphase component and is adapted to determine the concentration of a specific gas on the basis of the propagation time obtained through utilization of the modulation point present in the ultrasonic wave.

9. A gas concentration sensor according to claim 1, wherein the specific gas is vaporized fuel for use with an internal combustion engine.

10. A gas concentration sensor according to claim 1, wherein the specific gas is hydrogen gas.

11. A gas concentration sensor comprising:
    a measurement chamber having an inflow path for allowing inflow of gas under measurement thereinto and an outflow path for allowing outflow of the gas therefrom;
    an ultrasonic element disposed on one of two wall surfaces located in opposition to each other within said measurement chamber, and capable of transmitting an ultrasonic wave toward the other of the two wall surfaces and receiving an ultrasonic wave reflected from the wall surface serving as a reflection surface; and gas concentration detection means for causing said ultrasonic element to transmit an ultrasonic wave and to receive the reflected wave, for measuring a propagation time between transmission of the ultrasonic wave and reception of the reflected wave, and for determining a concentration of a specific gas contained in the gas under measurement on the basis of the propagation time, said sensor being characterized in that an area of the reflection surface of said measurement chamber is not less than an area of an opening surface of said ultrasonic element.

12. A gas concentration sensor according to claim 11, wherein a cross-sectional area of the outflow path is smaller than a cross-sectional area of the inflow path.

13. A gas concentration sensor according to claim 11, characterized in that said measurement chamber is formed such that an edge portion of the reflection surface is formed into a depression having a bottom surface parallel to the reflection surface and such that a distance between the bottom surface of the depression and said ultrasonic element is at least 18 mm greater than a distance between a central portion of the reflection surface and said ultrasonic element.

14. A gas concentration sensor according to claim 11, wherein said gas detection means causes said ultrasonic element to transmit an ultrasonic wave so that the ultrasonic wave is reflected from the reflection surface to thereby become a first reflected wave; said gas detection means causes said ultrasonic element to reflect the first reflected wave so that the first reflected wave is again reflected from the reflection surface; and said gas detection means measures a propagation time associated with a reflected wave other than the first reflected wave so as to determine the concentration of a specific gas on the basis of the propagation time.

15. A gas concentration sensor according to claim 11, wherein a bypass path for connecting the inflow path and the outflow path is provided separately from said measurement chamber.

16. A gas concentration sensor according to claim 11, wherein said gas concentration detection means measures a propagation time between reception of an ultrasonic wave by said ultrasonic element and next reception of an ultrasonic wave by said ultrasonic element and determines the concentration of a specific gas on the basis of the propagation time.

17. A gas concentration sensor according to claim 11, wherein said gas detection means causes said ultrasonic element to transmit/receive an ultrasonic wave involving at least one frequency modulation and is adapted to determine the concentration of a specific gas on the basis of the propagation time obtained through utilization of the modulation point present in the ultrasonic wave.

18. A gas concentration sensor according to claim 11, wherein said gas detection means causes said ultrasonic element to transmit/receive an ultrasonic wave involving at least one antiphase component and is adapted to determine the concentration of a specific gas on the basis of the propagation time obtained through utilization of the modulation point present in the ultrasonic wave.

19. A gas concentration sensor according to claim 11, wherein the specific gas is vaporized fuel for use with an internal combustion engine.

20. A gas concentration sensor according to claim 11, wherein the specific gas is hydrogen gas.

21. A gas concentration sensor comprising:

a measurement chamber having an inflow path for allowing inflow of gas under measurement thereinto and an outflow path for allowing outflow of the gas therefrom;

an ultrasonic element disposed on one of two wall surfaces located in opposition to each other within said measurement chamber, and capable of transmitting an ultrasonic wave toward the other of the two wall surfaces and receiving an ultrasonic wave reflected from the wall surface serving as a reflection surface; and gas concentration detection means for causing said ultrasonic element to transmit an ultrasonic wave and to receive the reflected wave, for measuring a propagation time between transmission of the ultrasonic wave and reception of the reflected wave through detection of a specific position in a waveform of the ultrasonic wave, and for determining a concentration of a specific gas contained in the gas under measurement on the basis of the propagation time, said sensor being characterized in that said measurement chamber is formed such that a distance between a central portion of the reflection surface and said ultrasonic element is at least 60 mm.

22. A gas concentration sensor according to claim 21, wherein a cross-sectional area of the outflow path is smaller than a cross-sectional area of the inflow path.

23. A gas concentration sensor according to claim 21, characterized in that said measurement chamber is formed such that an edge portion of the reflection surface is formed into a depression having a bottom surface parallel to the reflection surface and such that a distance between the bottom surface of the depression and said ultrasonic element is at least 18 mm greater than a distance between a central portion of the reflection surface and said ultrasonic element.

24. A gas concentration sensor according to claim 21, wherein said gas detection means causes said ultrasonic element to transmit an ultrasonic wave so that the ultrasonic wave is reflected from the reflection surface to thereby become a first reflected wave; said gas detection means causes said ultrasonic element to reflect the first reflected wave so that the first reflected wave is again reflected from the reflection surface; and said gas detection means measures a propagation time associated with a reflected wave other than the first reflected wave so as to determine the concentration of a specific gas on the basis of the propagation time.

25. A gas concentration sensor according to claim 21, wherein a bypass path for connecting the inflow path and the outflow path is provided separately from said measurement chamber.

26. A gas concentration sensor according to claim 21, wherein said gas concentration detection means measures a propagation time between reception of an ultrasonic wave by said ultrasonic element and next reception of an ultrasonic wave by said ultrasonic element and determines the concentration of a specific gas on the basis of the propagation time.

27. A gas concentration sensor according to claim 21, wherein said gas detection means causes said ultrasonic element to transmit/receive an ultrasonic wave involving at least one frequency modulation and is adapted to determine the concentration of a specific gas on the basis of the propagation time obtained through utilization of the modulation point present in the ultrasonic wave.

28. A gas concentration sensor according to claim 21, wherein said gas detection means causes said ultrasonic element to transmit/receive an ultrasonic wave involving at least one antiphase component and is adapted to determine the concentration of a specific gas on the basis of the propagation time obtained through utilization of the modulation point present in the ultrasonic wave.

29. A gas concentration sensor according to claim 21, wherein the specific gas is vaporized fuel for use with an internal combustion engine.

30. A gas concentration sensor according to claim 21, wherein the specific gas is hydrogen gas.

31. A gas concentration sensor comprising:
a measurement chamber having an inflow path for allowing inflow of gas under measurement thereinto and an outflow path for allowing outflow of the gas therefrom;
an ultrasonic element disposed on one of two wall surfaces located in opposition to each other within said measurement chamber, and capable of transmitting an ultrasonic wave toward the other of the two wall surfaces and receiving an ultrasonic wave reflected from the wall surface serving as a reflection surface; and
gas concentration detection means for causing said ultrasonic element to transmit an ultrasonic wave and to receive the reflected wave, for measuring a propagation time between transmission of the ultrasonic wave and reception of the reflected wave, and for determining a concentration of a specific gas contained in the gas under measurement on the basis of the propagation time,
said sensor being characterized in that a cross-sectional area of the outflow path is smaller than a cross-sectional area of the inflow path.

32. A gas concentration sensor according to claim 31, wherein said gas detection means causes said ultrasonic element to transmit an ultrasonic wave so that the ultrasonic wave is reflected from the reflection surface to thereby become a first reflected wave; said gas detection means causes said ultrasonic element to reflect the first reflected wave so that the first reflected wave is again reflected from the reflection surface; and said gas detection means measures a propagation time associated with a reflected wave other than the first reflected wave so as to determine the concentration of a specific gas on the basis of the propagation time.

33. A gas concentration sensor according to claim 31, wherein a bypass path for connecting the inflow path and the outflow path is provided separately from said measurement chamber.

34. A gas concentration sensor according to claim 31, wherein said gas concentration detection means measures a propagation time between reception of an ultrasonic wave by said ultrasonic element and next reception of an ultrasonic wave by said ultrasonic element and determines the concentration of a specific gas on the basis of the propagation time.

35. A gas concentration sensor according to claim 31, wherein said gas detection means causes said ultrasonic element to transmit/receive an ultrasonic wave involving at least one frequency modulation and is adapted to determine the concentration of a specific gas on the basis of the propagation time obtained through utilization of the modulation point present in the ultrasonic wave.

36. A gas concentration sensor according to claim 31, wherein said gas detection means causes said ultrasonic element to transmit/receive an ultrasonic wave involving at least one antiphase component and is adapted to determine the concentration of a specific gas on the basis of the propagation time obtained through utilization of the modulation point present in the ultrasonic wave.

37. A gas concentration sensor according to claim 31, wherein the specific gas is vaporized fuel for use with an internal combustion engine.

38. A gas concentration sensor according to claim 31, wherein the specific gas is hydrogen gas.

39. A gas concentration sensor comprising:
a measurement chamber having an inflow path for allowing inflow of gas under measurement thereinto and an outflow path for allowing outflow of the gas therefrom;
a pair of ultrasonic elements disposed respectively on two wall surfaces located in opposition to each other within said measurement chamber, and capable of transmitting/receiving an ultrasonic wave; and
gas concentration detection means for causing one of said ultrasonic elements to transmit an ultrasonic wave and the other of said ultrasonic elements to receive the ultrasonic wave, for measuring a propagation time between transmission of the ultrasonic wave and reception of the ultrasonic wave, and for determining a concentration of a specific gas contained in the gas under measurement on the basis of the propagation time,
said sensor being characterized in that a cross-sectional area of the outflow path is smaller than a cross-sectional area of the inflow path.

40. A gas concentration sensor according to claim 39, wherein a bypass path for connecting the inflow path and the outflow path is provided separately from said measurement chamber.

41. A gas concentration sensor according to claim 39, wherein said gas concentration detection means measures a propagation time between reception of an ultrasonic wave by said ultrasonic element and next reception of an ultrasonic wave by said ultrasonic element and determines the concentration of a specific gas on the basis of the propagation time.

42. A gas concentration sensor according to claim 39, wherein said gas detection means causes said ultrasonic element to transmit/receive an ultrasonic wave involving at least one frequency modulation and is adapted to determine the concentration of a specific gas on the basis of the propagation time obtained through utilization of the modulation point present in the ultrasonic wave.

43. A gas concentration sensor according to claim 39, wherein said gas detection means causes said ultrasonic element to transmit/receive an ultrasonic wave involving at least one antiphase component and is adapted to determine the concentration of a specific gas on the basis of the propagation time obtained through utilization of the modulation point present in the ultrasonic wave.

44. A gas concentration sensor according to claim 39, wherein the specific gas is vaporized fuel for use with an internal combustion engine.

45. A gas concentration sensor according to claim 39, wherein the specific gas is hydrogen gas.

* * * * *